(12) United States Patent
Feldman et al.

(10) Patent No.: US 12,023,482 B2
(45) Date of Patent: *Jul. 2, 2024

(54) COMPLIANCE VOLTAGE MONITORING AND ADJUSTMENT IN AN IMPLANTABLE MEDICAL DEVICE

(71) Applicant: Boston Scientific Neuromodulation Corporation, Valencia, CA (US)

(72) Inventors: Emanuel Feldman, Simi Valley, CA (US); Goran N. Marnfeldt, Valencia, CA (US); Kenneth Hermann, Santa Clara, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 17/654,280

(22) Filed: Mar. 10, 2022

(65) Prior Publication Data
US 2022/0193394 A1 Jun. 23, 2022

Related U.S. Application Data

(63) Continuation of application No. 16/701,916, filed on Dec. 3, 2019, now Pat. No. 11,273,303, which is a (Continued)

(51) Int. Cl.
*A61N 1/02* (2006.01)
*A61N 1/05* (2006.01)
(Continued)

(52) U.S. Cl.
CPC .............. *A61N 1/025* (2013.01); *A61N 1/05* (2013.01); *A61N 1/36* (2013.01); *A61N 1/36125* (2013.01);
(Continued)

(58) Field of Classification Search
CPC . A61N 1/025; A61N 1/05; A61N 1/36; A61N 1/36153; A61N 1/37
See application file for complete search history.

(56) References Cited

U.S. PATENT DOCUMENTS 6,181,969 B1  1/2001  Gord
6,516,227 B1  2/2003  Meadows et al.
(Continued)

OTHER PUBLICATIONS

International Search Report and Written Opinion regarding corresponding PCT Application No. PCT/US2017/050300, dated Nov. 20, 2017.

*Primary Examiner* — Joseph M Dietrich
(74) *Attorney, Agent, or Firm* — Lewis & Reese, PLLC

(57) ABSTRACT

An architecture is disclosed for an Implantable Pulse Generator having improved compliance voltage monitoring and adjustment software and hardware. Software specifies which stimulation pulses are to be measured as relevant to monitoring and adjusting the compliance voltage. Preferably, specifying such pulses occurs by setting a compliance monitoring instruction (e.g., a bit) in the program that defines the pulse, and the compliance monitor bit instruction may be set at a memory location defining a particular pulse phase during which the compliance voltage should be monitored. When a compliance monitor instruction issues, the active electrode node voltages are monitored and compared to desired ranges to determine whether they are high or low. Compliance logic operates on these high/low signals and processes them to decide whether to issue a compliance voltage interrupt to the microcontroller, which can then command the compliance voltage generator to increase or decrease the compliance voltage.

20 Claims, 16 Drawing Sheets

Related U.S. Application Data continuation of application No. 15/696,005, filed on Sep. 5, 2017, now Pat. No. 10,525,252.

(60) Provisional application No. 62/425,765, filed on Nov. 23, 2016, provisional application No. 62/386,000, filed on Sep. 10, 2016.

(51) Int. Cl.
    *A61N 1/36*      (2006.01)
    *A61N 1/37*      (2006.01)
    *A61N 1/39*      (2006.01)

(52) U.S. Cl.
    CPC ............ *A61N 1/36153* (2013.01); *A61N 1/37* (2013.01); *A61N 1/3925* (2013.01)

(56) References Cited

U.S. PATENT DOCUMENTS

| | | |
|---|---|---|
| 6,553,263 B1 | 4/2003 | Meadows et al. |
| 7,127,298 B1 | 10/2006 | He et al. |
| 7,177,698 B2 | 2/2007 | Klosterman et al. |
| 7,444,181 B2 | 10/2008 | Shi et al. |
| 7,539,538 B2 | 5/2009 | Parramon et al. |
| 7,623,916 B2 | 11/2009 | Julian |
| 7,801,600 B1 | 9/2010 | Carbunaru et al. |
| 7,801,602 B2 | 9/2010 | McClure et al. |
| 7,805,189 B2 | 9/2010 | Stein et al. |
| 7,872,884 B2 | 1/2011 | Parramon et al. |
| 7,881,803 B2 | 2/2011 | Parramon et al. |
| 7,890,182 B2 | 2/2011 | Parramon et al. |
| 8,219,196 B2 | 7/2012 | Torgerson |
| 8,606,362 B2 | 12/2013 | He et al. |
| 8,620,436 B2 | 12/2013 | Parramon et al. |
| 8,649,858 B2 | 2/2014 | Griffith et al. |
| 8,768,453 B2 | 7/2014 | Parramon et al. |
| 9,002,465 B2 | 4/2015 | Ranu |
| 9,008,790 B2 | 4/2015 | Griffith et al. |
| 9,037,241 B2 | 5/2015 | Lamont et al. |
| 9,061,140 B2 | 6/2015 | Shi et al. |
| 9,155,891 B2 | 10/2015 | Archer |
| 9,174,051 B2 | 11/2015 | Marnfeldt et al. |
| 9,220,901 B2 | 12/2015 | Gururaj et al. |
| 9,233,254 B2 | 1/2016 | Nimmagadda et al. |
| 9,259,574 B2 | 2/2016 | Aghassian et al. |
| 9,308,373 B2 | 4/2016 | Lee |
| 9,314,632 B2 | 4/2016 | Marnfeldt et al. |
| 9,327,135 B2 | 5/2016 | Vansickle et al. |
| 9,352,162 B2 | 5/2016 | Lamont et al. |
| 9,397,639 B2 | 7/2016 | Feldman et al. |
| 10,420,935 B2 | 9/2019 | Illegems et al. |
| 10,525,252 B2 * | 1/2020 | Feldman ................ A61N 1/025 |
| 11,273,303 B2 * | 3/2022 | Feldman .................. A61N 1/36 |
| 2006/0173493 A1 | 8/2006 | Armstrong et al. |
| 2008/0114231 A1 | 5/2008 | Dai et al. |
| 2009/0062883 A1 | 3/2009 | Meadows et al. |
| 2010/0268309 A1 | 10/2010 | Parramon et al. |
| 2012/0095529 A1 | 4/2012 | Parramon et al. |
| 2013/0073008 A1 | 3/2013 | Ternes et al. |
| 2013/0184794 A1 | 7/2013 | Feldman et al. |
| 2013/0289665 A1 | 10/2013 | Marnfeldt et al. |
| 2013/0310897 A1 | 11/2013 | Marnfeldt et al. |
| 2015/0066108 A1 | 3/2015 | Shi et al. |
| 2015/0134029 A1 | 5/2015 | Ozawa et al. |
| 2015/0144183 A1 | 5/2015 | Yang et al. |
| 2015/0157861 A1 | 6/2015 | Aghassian |
| 2015/0360038 A1 | 12/2015 | Zottola et al. |
| 2016/0051825 A1 | 2/2016 | Ter-Petrosyan et al. |
| 2018/0071511 A1 | 3/2018 | Marndeldt et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |

* cited by examiner

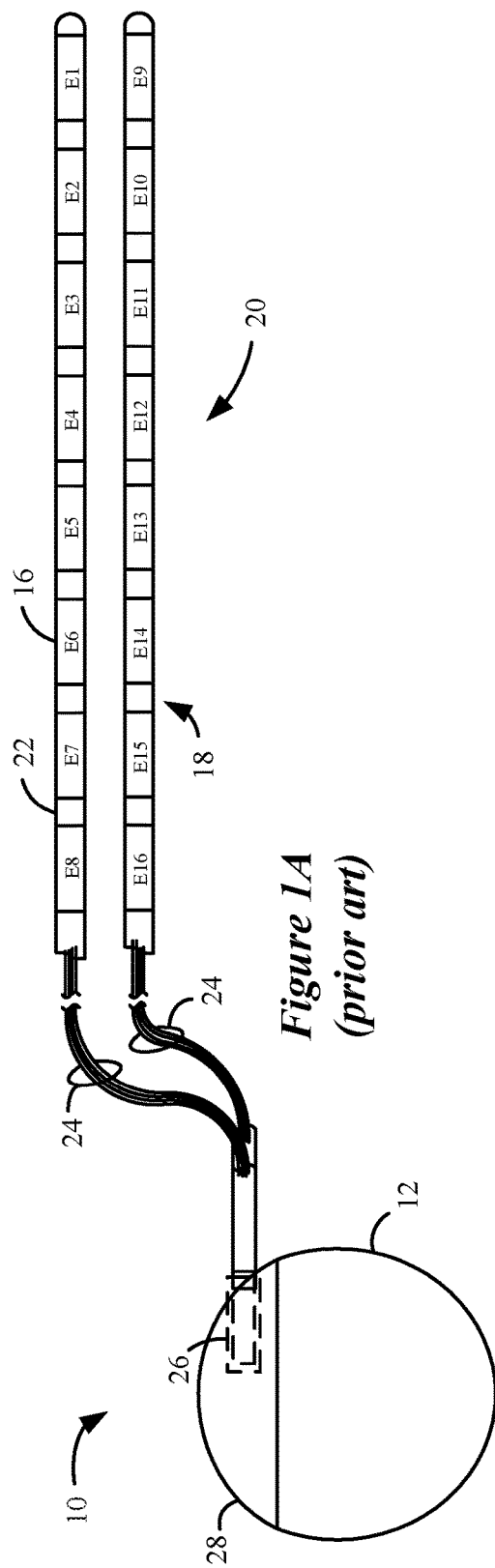
*Figure 1A (prior art)*
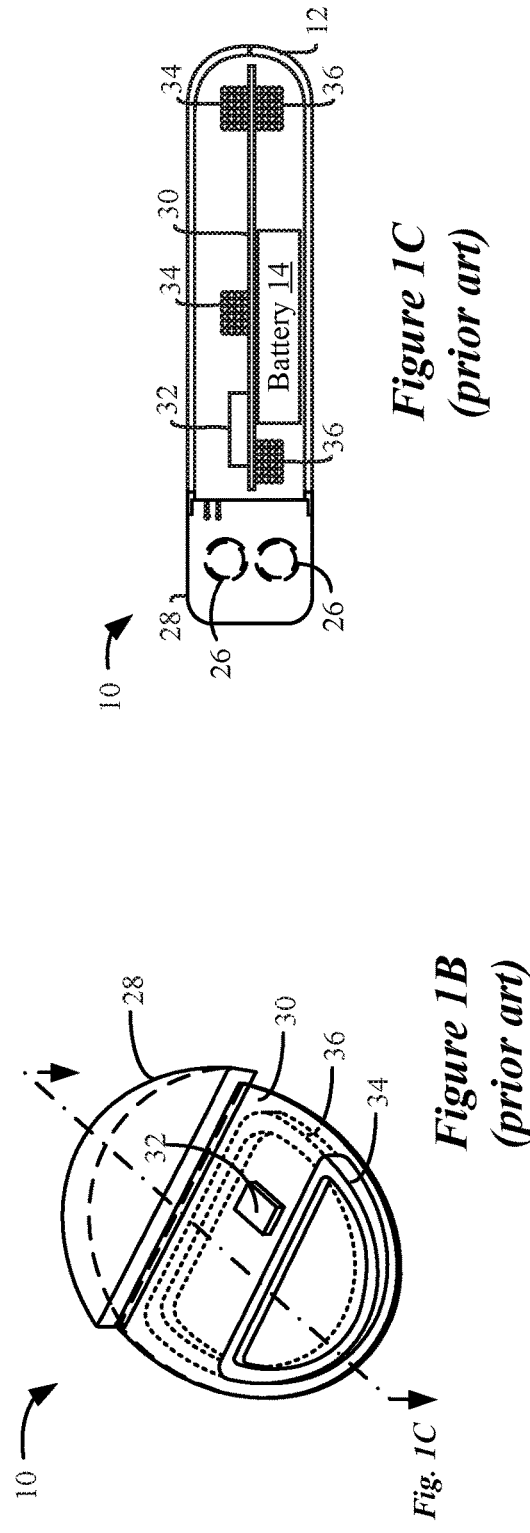
*Figure 1B (prior art)*
*Figure 1C (prior art)*

COMPLIANCE VOLTAGE MONITORING AND ADJUSTMENT IN AN IMPLANTABLE MEDICAL DEVICE

CROSS-REFERENCE TO RELATED APPLICATIONS

This is a continuation application of U.S. patent application Ser. No. 16/701,916, filed Dec. 3, 2019 (allowed), which is a continuation application of U.S. patent application Ser. No. 15/696,005, filed Sep. 5, 2017 (now U.S. Pat. No. 10,525,252), which is a non-provisional application based on United States Provisional Patent Application Ser. Nos. 62/425,765, filed Nov. 23, 2016, and 62/386,000, filed Sep. 10, 2016. These applications are incorporated by reference in their entireties, and priority is claimed.

FIELD OF THE INVENTION

The present invention relates generally to implantable medical devices, and more particularly to improved compliance voltage monitoring and adjustment in an implantable pulse generator.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10, which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIGS. 2A and 2B show an architecture 140 for the circuitry in IPG 10, which is disclosed in U.S. Pat. No. 10,576,265 ("the '265 patent") and U.S. Pat. No. 11,040,192 ("the '192 patent"), both of which are incorporated by reference in their entireties. Architecture 140 includes at least one Application Specific Integrated Circuit (ASIC) 160. ASIC 160 includes a microcontroller block 150, which as shown in FIG. 2B can communicate with other functional blocks in the ASIC 160 via internal bus 192. Because ASIC 160 includes an internal microcontroller 150, an external microcontroller can be dispensed with in the improved architecture 140, simplifying IPG design and saving room within the interior of the case 12 and on the IPG's PCB 30 (FIG. 1C). In one example, the microcontroller block 150 can comprise circuitry from an ARM Cortex-M0+ Processor, which may be incorporated into the monolithic integrated circuit of the ASIC 160 by licensing various necessary circuits from the library that comprises that processor. ASIC 160 can comprise a monolithic integrated circuit formed on its own semiconductive substrates ("chip"), and may be contained in its own package and mounted to the IPG 10's PCB 30.

Even though ASIC 160 includes a microcontroller block 150, the ASIC 160 may still couple to an external bus 190. This can facilitate communications between the ASIC 160 and another device, such as a memory integrated circuit (not shown) or possibly another microcontroller device that might be coupled to the bus 190 as explained in the above-incorporated '265 and '192 patents. External bus 190 can also facilitate communication between (master) ASIC 160 and another identically-constructed (slave) ASIC 160', shown in dotted lines in FIG. 2A. Use of an additional ASIC 160' allows the number of electrodes 16 the IPG 10 supports to be doubled, for example from sixteen to thirty two, or thirty two to sixty four. Off-bus connections 54 can facilitate master/slave interaction between ASICs 160 and 160', and as explained in detail in the above-incorporated '265 and '192 patents.

FIG. 2B shows various functional circuit blocks within ASIC 160 in addition to the microcontroller block, which are briefly described. As mentioned, ASIC 160 includes an internal bus 192, and each of the functional blocks includes interface circuitry 88 enabling communication on the internal bus 192. Interface circuitry 88 helps each block recognize when microcontroller block 150 is communicating addresses pertaining to that block via bus 192.

ASIC 160 contains several terminals 61 (e.g., pins, bond pads, solder bumps, etc.), such as those necessary to connect to the external bus 190, the battery 14, the coils 34, 36, external memory (not shown), etc. ASIC terminals 61 include electrode nodes 61a (E1'-E16' and Ec') which circuit nodes are also present on the PCB 30 (FIG. 1C) inside of the IPG's case 12. The electrode nodes 61a connect to the electrodes 16 (E1-E16) on the lead(s) 18 outside of the case 12 by way of DC-blocking capacitors 55. As is known, DC-blocking capacitors 55 are useful to ensure that DC current isn't inadvertently (e.g., in the event of failure of the ASIC 160's circuitry) injected into the patient's tissue, and hence provide safety to the IPG 10. Such DC-blocking capacitors 55 can be located on or in the IPG 10's PCB 30. See U.S. Patent Application Publication 2015/0157861. Note that there is also an electrode node 61a Ec' which is connected to the case 12 (preferably by a DC-blocking capacitor 55), thus allowing the case 12 to operate as an electrode 16 (Ec). ASIC 160 may support other numbers or types of electrode nodes/electrodes (e.g., thirty-two electrodes E1-E32 plus the case Ec).

Each of the circuit blocks in ASIC 160 performs various functions in IPG 10. Telemetry block 64 couples to the IPG telemetry coil 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat, the compliance voltage VH (discussed in detail below), or voltages appearing at the electrodes, and is coupled to an analog bus 67 containing such voltages. A/D block 66 may further receive signals from sample and hold block 68. For example, sample and hold circuitry 68 may determine a voltage difference between two electrode nodes, which voltage difference may then be digitized at A/D block 66. Knowing the difference in voltage between two electrodes when they pass a constant current allows for a determination of the (tissue) resistance between them, which is useful for a variety of reasons.

Clock generation block 74 can be used to generate a clock for the ASIC 160 and communication on the bus 192. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 160.

Master/slave control block 86 can be used to inform the ASIC 160 whether it is to be used as a master ASIC or as a slave ASIC (e.g., 160 or 160' in FIG. 2A), which may be bond programmed at M/S terminal 61. For example, M/S terminal may be connected to a power supply voltage (e.g., Vbat) to inform ASIC 160 that it will operate as a master ASIC, or to ground to inform that it will operate as a slave 160', in which case certain functional blocks will be disabled, as the above-cited references explain.

Nonvolatile memory (NOVO) block 78 caches any relevant data in the system (such as log data). Additional memory (not shown) can also be provided off-chip via a serial interface block 84.

ASIC 160 further includes a stimulation circuitry block 170 (FIG. 2B), which includes circuitry for receiving and storing stimulation parameters from the microcontroller block 150 via bus 192. Stimulation parameters define the shape and timing of stimulation pulses to be formed at the electrodes, and can include parameters such as which electrodes E1-E16 or Ec will be active; whether those active electrodes are to act as anodes that source current to a patient's tissue, or cathodes that sink current from the tissue; and the amplitude (A), duration (D), and frequency (f) of the pulses. Amplitude may comprise a voltage or current amplitude. Such stimulation parameters may be stored in registers in the stimulation circuitry block 170. See, e.g., U.S. Patent Application Publications 2013/0289661; 2013/0184794.

Simulation circuitry block 170 also includes a Digital-to-Analog Converter (DAC) 172 for receiving the stimulation parameters from the registers and for forming the prescribed pulses at the selected electrodes. FIG. 3 shows a simple example of DAC circuitry 172 operating to provide current pulses between selected electrodes E1 and E2 and through a patient's tissue, Rt. DAC circuitry 172 as shown comprises two portions, denoted as PDAC 172p and NDAC 172n. These portions of DAC circuitry 172 are so named because of the polarity of the transistors used to build them and the polarity of the currents they provide. Thus, PDAC 172p is formed primarily from P-channel transistors and is used to source a current+I to the patient's tissue Rt via a selected electrode E1 operating as an anode. NDAC 172n is formed primarily from N-channel transistors and is used to sink current −I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 172p and NDAC 172n receive digital control signals from the registers in the stimulation circuitry block 170, generically denoted <Pstim> and <Nstim> respectively, to generate the prescribed pulses with the prescribed timing and amplitude. In the example shown, PDAC 172p and NDAC 172n comprise current sources, but could comprise voltage sources as well. The DAC circuitry 172 (PDAC 172p and NDAC 172n) may be dedicated at each of the electrodes, and thus may be activated only when its associated electrode is selected as an anode or cathode. See, e.g., U.S. Pat. No. 6,181,969. Alternatively, the current produced by one or more DACs (or one or more current sources or sinks within a DAC) may be distributed to a selected electrode by a switch matrix (not shown), in which case optional control signals <Psel> and <Nsel> would be used to control the switch matrix and establish the connection between the selected electrode and a current source or sink. See, e.g., U.S. Pat. No. 8,606,362. DAC circuitry 172 may also use a combination of these dedicated and distributed approaches. See, e.g., U.S. Pat. No. 8,620,436.

The PDAC 172p and NDAC 172n along with the intervening tissue Rt complete a circuit between a power supply VH, called the compliance voltage, and ground. The compliance voltage VH is preferable adjustable to an optimal level at compliance voltage generator block 76 (FIG. 2B) to ensure that current pulses of a prescribed amplitude can be produced without unnecessarily wasting IPG power. Such adjustment may occur by measuring voltage drops across the PDAC (Vp) and NDAC (Vn) circuitry as they are forming a pulse. The measured voltage drops can be used to ensure that the compliance voltage VH produced is optimal for the stimulation current being provided—i.e., VH is not too low to be unable to produce the current required for the stimulation, nor too high so as to waste power in the IPG 10. Compliance voltage generator block 76 includes circuitry for boosting a power supply voltage such as the battery voltage, Vbat, to a proper level for VH. Such boost circuitry (components of which may be located off chip) can include an inductor-based boost converter or a capacitor-based charge pump.

In the example waveform shown in FIG. 3, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., of the area under the first and second pulse phases are equal). Recovery of excess charge on the DC-blocking capacitors 55 is desirable to ensure that the DAC circuitry 172 will operate as intended: if the charge across the DC-blocking capacitors 55 is not zero at the end of each pulse, such remaining charge may impact formation of subsequent pulses, or other problems may occur, as discussed further below.

While active recovery of charge using a biphasic pulse is beneficial, such active recovery may not be perfect, and hence some residual charge may remain on the DC-blocking capacitors 55 even after completion of the second phase 94b of the biphasic pulse. Passive charge recovery may therefore be employed that does not involve use of active currents provided by the DAC circuitry 172. Passive charge recovery is implemented within the stimulation circuitry block 170, and includes use of passive recovery switches (e.g., transistors) 96(x), each connected between one of the electrode nodes (Ex' and Ec') 61a and a common reference voltage. This common reference voltage as shown may simply comprise the voltage, Vbat, of the battery 14 as (FIG. 1C) as shown, but another reference voltage could also be used, such as the compliance voltage VH described earlier, a midpoint voltage such as VH/2, ground (GND), or some other value. A variable resistor 97 is connected in series to each of the passive recovery switches 96 between the electrodes nodes 61a and the common reference voltage (e.g., Vbat) to set the rate of passive discharge. See e.g., U.S. Pat. No. 10,716,937 ("the '937 patent") (discussing advents related to passive recovery).

BRIEF DESCRIPTION OF THE DRAWINGS

FIGS. 1A-1C show an Implantable Pulse Generator (IPG), and the manner in which an electrode array is coupled to the IPG, in accordance with the prior art.

FIG. 5A shows a pulse train issued according to a first aggregate program (FIG. 5C) associating a pulse program and a steering program (FIG. 5B) in a first timing channel, while

DETAILED DESCRIPTION

Before discussing compliance voltage monitoring and adjustment, which are the focus of this disclosure, further details concerning the stimulation circuitry 170 and its DAC circuitry 172 are shown in FIGS. 4A-4D. This is done for completeness, and to show an example implementation in which the compliance voltage monitoring and adjustment aspects of this disclosure can operate. Still further details concerning these circuitries can be found in the above-incorporated '265 and '192 patents, with which the reader is assumed familiar. Note however that implementations of the invention are not limited to any particular stimulation circuitry 170 or DAC circuitry 172 implementation.

Figure 4A:
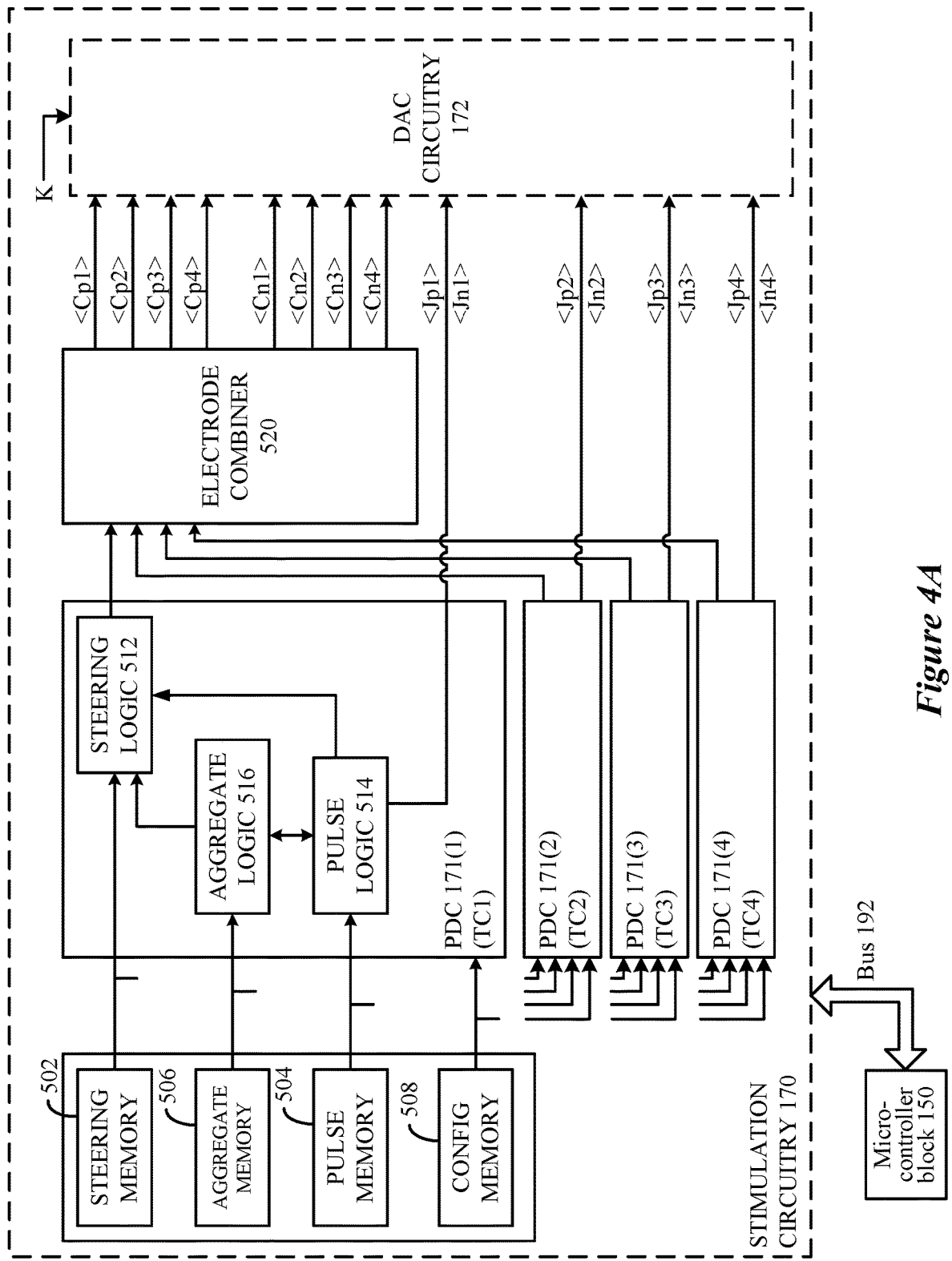
FIGS. 4A-4D show further details of the stimulation circuitry and DAC circuitry.

As shown in FIG. 4A, stimulation circuitry 170 includes memory circuitry that stores microcode processed by one or more pulse definition circuits (PDCs) 171, which operate as control circuits to generate the control signals that are sent to the DAC circuitry 172. Memory circuitry includes a steering memory 502 that contains electrode steering programs, and a pulse memory 504 that contains pulse programs, both of which are discussed further with respect to FIG. 5B. Memory circuitry also includes an aggregate memory 506 that contains aggregate programs that link or associate one or more pulse programs and one or more steering programs to create a desired stimulation pulse therapy program, as discussed further with respect to FIG. 5C. The stimulation circuitry 170 additionally includes a configuration memory 508 that stores configuration parameters, some of which are global and applied across all PDCs 171, and some of which are specific to a particular PDC 171. The memories 502, 504, 506, and 508 can be read from and written to by the microcontroller 150. Each location (e.g., each 32-bit location) in the memory circuitry may be formed as a register of multiple flip-flops or as an addressable location in a more typical memory, and may comprise separate memory circuits or a single memory circuit.

Stimulation circuitry 170, as well as comprising memory circuitry, can comprise logic circuitry. Such logic circuitry may include standard logic processing circuitry, such as CMOS logic gates, Arithmetic Logic Unit (ALU) circuitry, Digital Signal Processing (DSP) circuitry, Programmable Logic Array (PLA) circuitry, Field Programmable Gate Array (FPGA) circuitry, etc. Programming of such logic circuitry—i.e., algorithms operable in the stimulation circuitry 170 and the compliance logic 220 as described herein (FIG. 6A)—may comprise microcode or firmware that can be read and processed by such logic circuitry.

Each of the PDCs 171(1)-(4) are used in a normal mode (in which control signal K='0') to control the formation of stimulation pulses within a timing channel, and hence stimulation circuitry 170 as shown in FIG. 4A supports four such timing channels (TC1-TC4). As explained in further detail in the '265 patent, pulse logic 514 in each PDC 171(x) creates pulse amplitude control signals <Jpx> and <Jnx>, which are sent to the DAC circuitry 172. More specifically, and referring to FIG. 4B, pulse amplitude control signals <Jpx> and <Jnx> are respectively sent by a PDC171(x) to a particular PDACx/NDACx pair associated with each PDCx/timing channel (TCx) to set the magnitude of the pulses that are respectively sourced to or sunk from the electrodes selected in that timing channel. Thus, PDAC1 receives <Jp1> to set the amplitude of current sourced in timing channel 1 (TC1), while NDAC1 receives <Jn1> to set the amplitude of current sunk in TC1. Likewise, PDAC2 receives <Jp2> to set the amplitude of current sourced in TC2, while NDAC2 receives <Jn2> to set the amplitude of current sunk in TC2, etc. <Jpx> and <Jnx> within a timing channel may comprise the same value, and may be more simply referred to as <Jx>

Referring again to FIG. 4A, which electrodes are selected in each timing channel are determined using steering logic 512 (which reads data from the steering memory 502), aggregate logic 516 (which reads data from the aggregate memory 506), and the pulse logic 514. This will be described later with respect to FIGS. 5B and 5C. Ultimately, the steering logic 512 in each PDC 171 outputs to an electrode combiner 520 which determines which switches 178 (FIGS. 4C and 4D) are to be closed in which PDACs and NDACs. Specifically, the electrode combiner 520 issues switch control signals <Cpx> for the PDACx associated with PDC 171(x)/TCx, and switch control signals <Cnx> for the NDACx associated with PDC 171(x)/TCx, as shown in FIG. 4B.

Figure 4B:
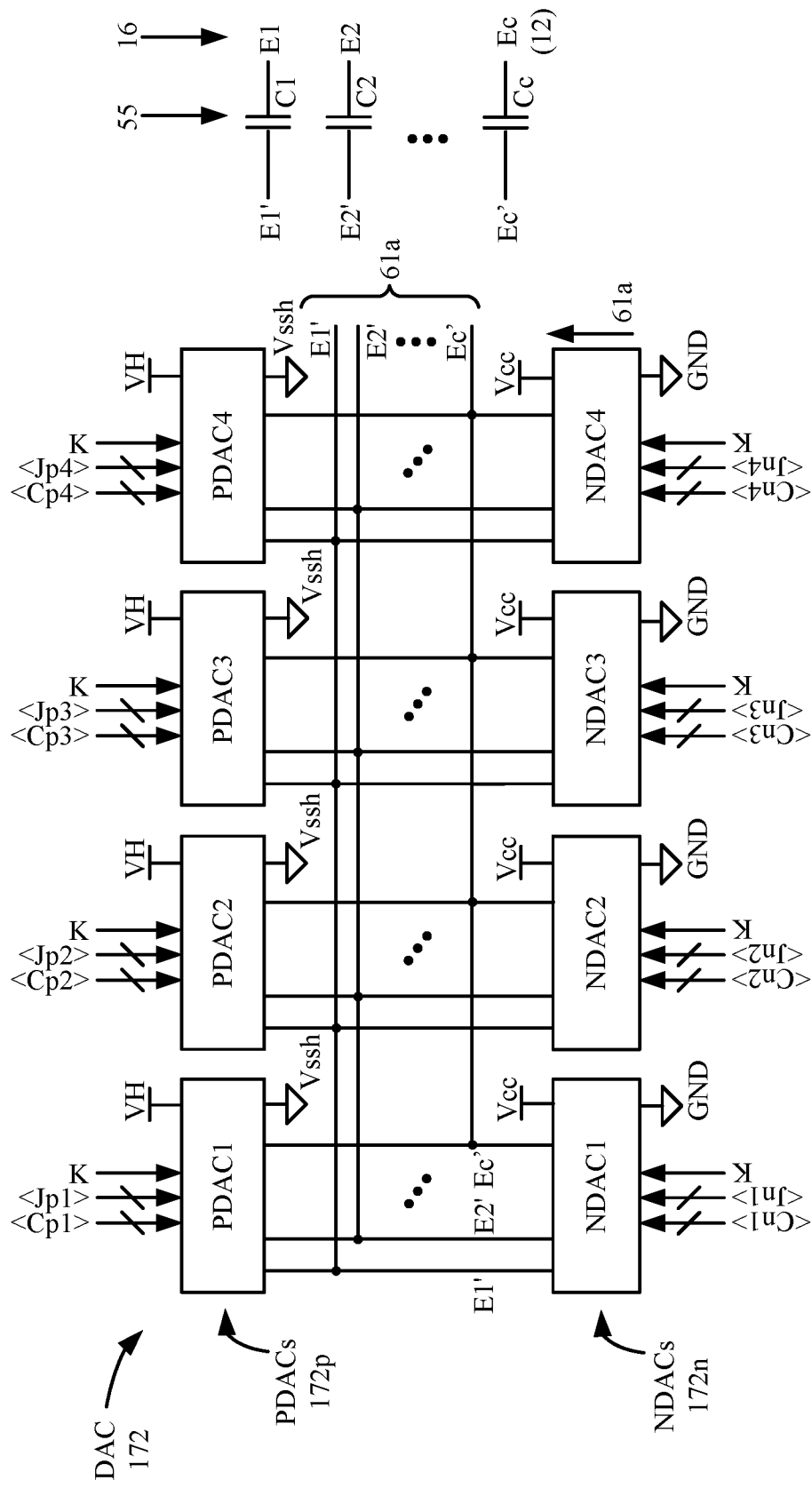

To summarize, in a normal mode (K=0), and as shown in FIG. 4B, the DAC circuitry 172, which constitutes PDAC circuitry 172p and NDAC circuitry 172, is organized into PDACx/NDACx pairs, each for producing stimulation pulses in a timing channel TCx. While four pairs/timing channels are shown in FIG. 4B, more or less could be supported. Notice that each PDAC and NDAC outputs to and is connected to the electrode nodes 61a. These electrode node outputs 61a are in turn connected to the electrodes 16 (e.g., E1-E16 and Ec) via DC-blocking capacitors 55 as described earlier. Note further that the PDACs are powered by power supply voltages VH (the compliance voltage that is the focus of this disclosure) and Vssh, which respectively define upper and lower power supply voltages for the PDACs, while the NDACs are powered by power supply voltages Vcc and ground (GND), which respectively define upper and lower power supply voltages for the NDACs. The benefits provided by these different power supply domains is discussed further in U.S. Pat. No. 10,786,665 ("the '665 patent"), and are not discussed further.

Figure 4C:
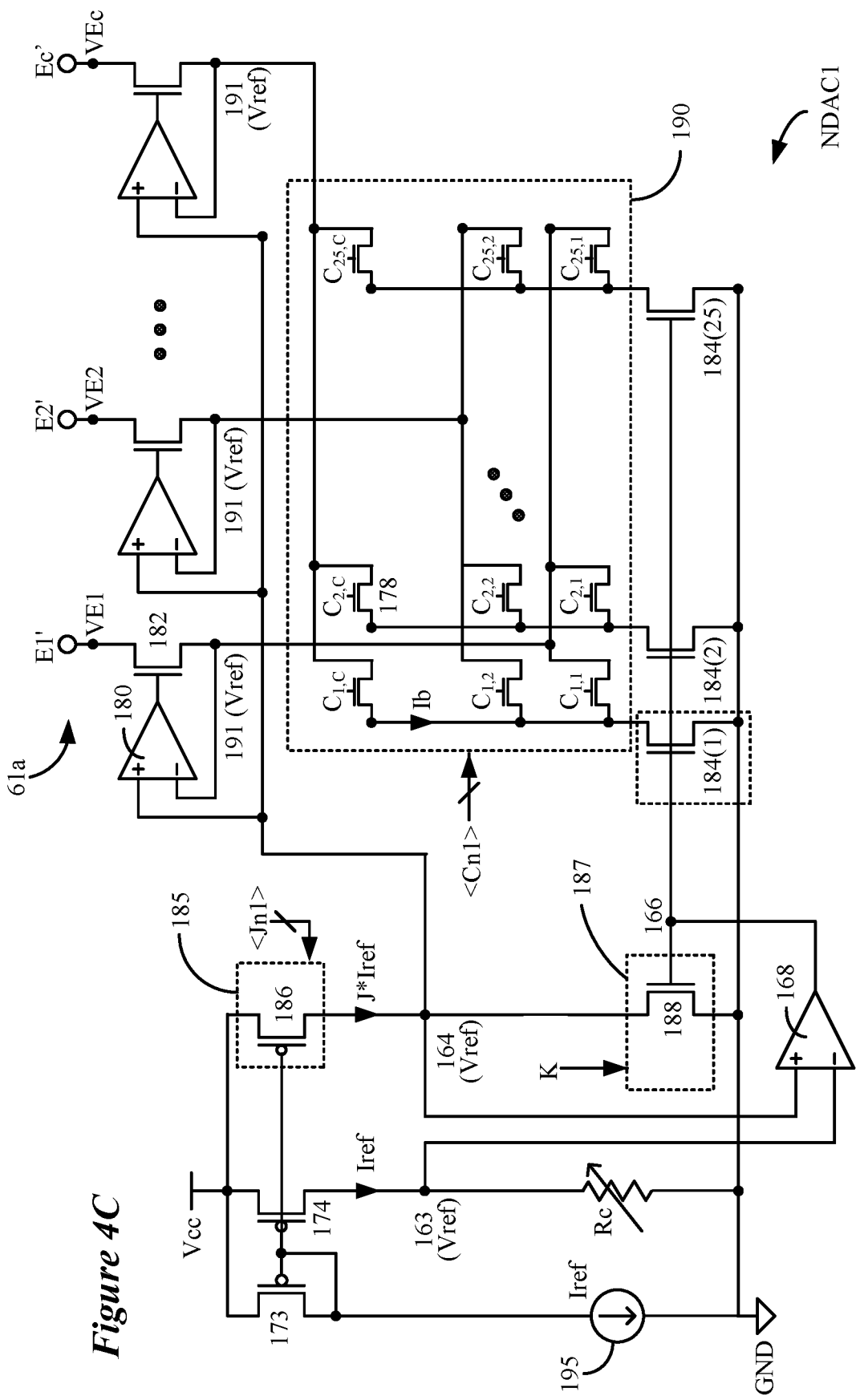
Figure 4D:
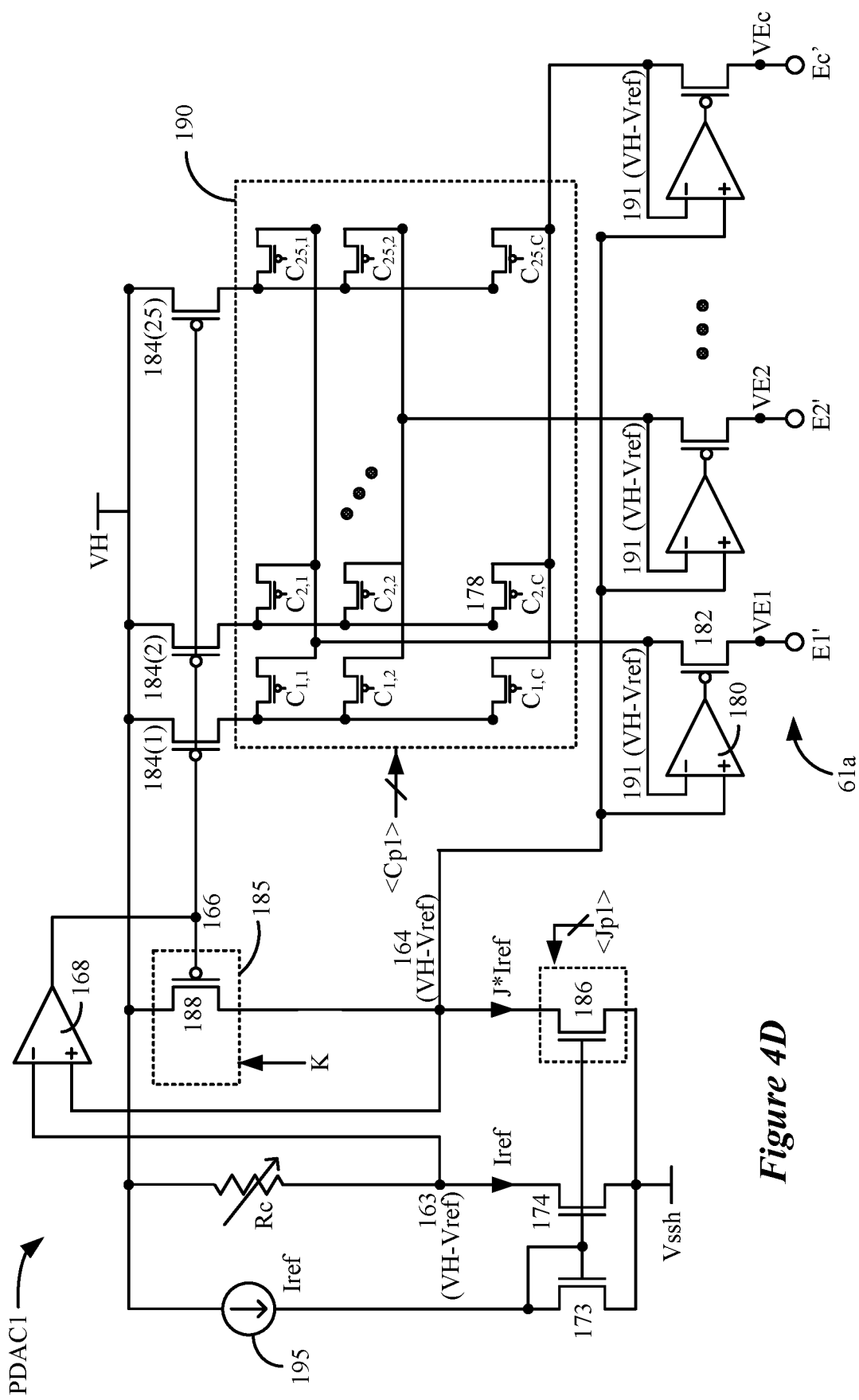

FIG. 4C shows circuitry for one of the NDACs (NDAC1), while FIG. 4D shows circuitry for one of the PDACs (PDAC1); circuitry for the other PDACs and NDACs are similar. As one skilled in the art will appreciate, the circuitry for PDACs is largely "inverted" from that shown for the NDACs, and has expected differences given its difference in polarity. For example, current-producing portions of the PDACs are coupled to the compliance voltage VH, thus allowing the PDACs to source current to selected electrode nodes 61a, and allowing their associated electrodes 16 to operate as anodes (positive current). By contrast, current-producing portions of the NDACs are coupled to ground, thus allowing the NDACs to sink current to selected electrode nodes 61a, and allowing their associated electrodes 16 to operate as cathodes (negative current). Further, many of the transistors in the PDACs comprise P-channel devices, while these same transistors in the NDACs comprise N-channel devices. Otherwise, the PDACs and NDACs function similarly, and are controlled by analogous control signals such as <Jpx>, <Cpx>, and <Jnx> and <Cnx>, and K. (Given the difference in transistor polarities, these control signals may be active at different logic state in the PDACs and the NDACs). For simplicity, elements of the PDACs in FIG. 4D are labeled with elements numerals that correspond to analogous elements in the NDACs of FIG. 4C.

The NDACs of FIG. 4C operates as follows. A reference current, Iref is mirrored by a current-mirror configuration from transistor 173 to transistor 174, where it is passed through a reference transistor, Rc, thus forming a reference voltage Vref (=Iref*Rc) at node 163. As explained in the above-incorporated '192 patent, reference transistor Rc may be adjustable to allow reference voltage Vref to be set. Preferably, Vref may equal 100 mV.

Iref is further mirrored to a master DAC 185, which amplifies Iref times a value J set by control signals <Jn1>. <Jn1> may comprise 8 control signals, therefore allowing J to be set from 1<00000001> to 255<11111111>. As explained in the '192 patent, J sets the number of transistors 186 in the master DAC 185 into which Iref is mirrored. Amplified current J*Iref passes to a resistance block 187, with is formed of one or more resistance transistors 188, and controlled by control signal K. As explained in the '192 patent, control signal K can be used to set a resolution of the current producible by the NDAC (and PDAC), but this detail can be ignored here.

The gate of resistance transistor(s) 188 is shared at node 166 as the gate of a number of branch transistors 184; 25 branch transistors 184 are shown in the example of FIG. 4C, although this number could be varied. Node 166 comprises the output of an operation amplifier ("op amp") 168. One of the inputs to op amp comprises node 163 (Vref). The other input, node 164, is coupled to the output node 166 by feedback through the resistance block 187. Hence, the op amp 168 will force its inputs to be equal such that node 164 will be forced to equal node 163, and thus node 164 is set to Vref.

A switch matrix 190 is connected between the branch transistors 184 and an output transistors 182 connected to each electrode node 61a. The switch matrix 190, comprising an array of switches (transistors) 178, can connect the current from any branch transistor 184 to any of the electrode nodes 61a and hence to the electrodes 16. Such connection is established via switch matrix control signals <Cn1>. For example, asserting control signal $C_{2,1}$ connects the second branch transistor 184(2) to electrode node E1'.

Each output transistors 182 is controlled by its own op amp 180. One input of op amp 180 is connected to node 164, which as explained earlier is forced to Vref. Given the feedback through each output transistor 182, the other inputs 191 are also forced to Vref. Vref is thus impressed across the branch transistors 184 when a switch coupled to that branch transistor is asserted; perhaps more importantly, Vref is impressed across both the resistance transistor(s) 188 and the branch transistor 184. These transistors 184 and 188 are also on to the same extent by virtue of their common gate connection at node 166. As such, the current through each branch transistors 184, Ib, will scale with the current through the resistance transistor(s) 188, J*Iref. More particularly, Ib will scale in accordance with the effective width of the transistors 184 and 188. For example, if resistance transistor(s) 188 have an effective width W1, and branch transistors 184 have a longer effective width W2, the current through the resistance transistor(s) 188 (J*Iref) will be amplified through each branch transistor 184: Ib=(W2/W1)*J*Iref.

The current from more than one branch transistor 184 can be summed at an electrode node if more than one switch matrix control signal <Cn1> associated with that electrode node is asserted; for example, if $C_{1,1}$, $C_{2,1}$, and $C_{3,1}$ are asserted, the branch current Ib from branch transistors 184(1), 184(2), and 184(3) will sum at electrode node E1'. Generally speaking, if L switches 178 associated with an electrode node are asserted, the current at that electrode node will be I=(W2/W1)*L*J*Iref.

Again, operation of the PDACs (FIG. 4D) is largely similar, with some noteworthy differences. First, the power supply used in the PDACs—VH and Vssh—create a reference voltage at nodes 163, 164, and 191 equal to VH-Vref, which difference can again equal 100 mV. Because the compliance voltage VH can change—as discussed previously, and discussed in further detail below—this reference voltage will change. Vssh will also change to keep VH-Vssh to a constant difference, and control signals used to control the PDACs will comprise logic states of VH ('1') and Vssh ('0'), which will likewise vary as VH changes. This is explained in detail in the above-referenced '665 patent.

From the perspective of the electrode nodes 61a, the PDACs will source a positive current, while the NDACs will sink a negative current. Note that a voltage (VE1, VE2, ... VEc) will form at the electrode nodes 61a when a particular electrode node is connected to a PDAC and being used to source current (as an anode) or is connected to an NDAC to sink current (as a cathode). As explained further below, these electrode node voltages will be used to monitor and potentially adjust the magnitude of the compliance voltage VH being generated.

Figure 5A:
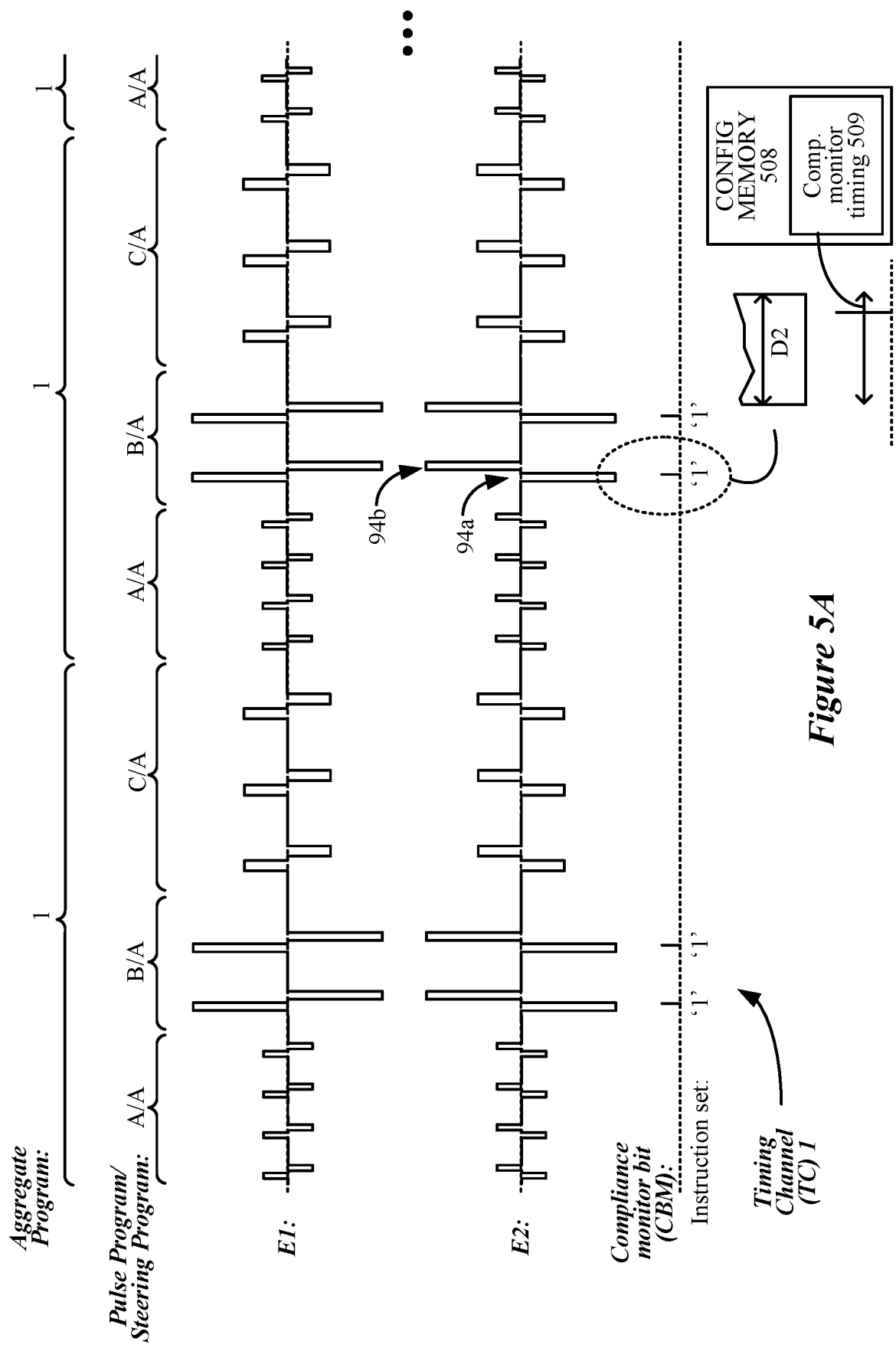
Figure 5B:
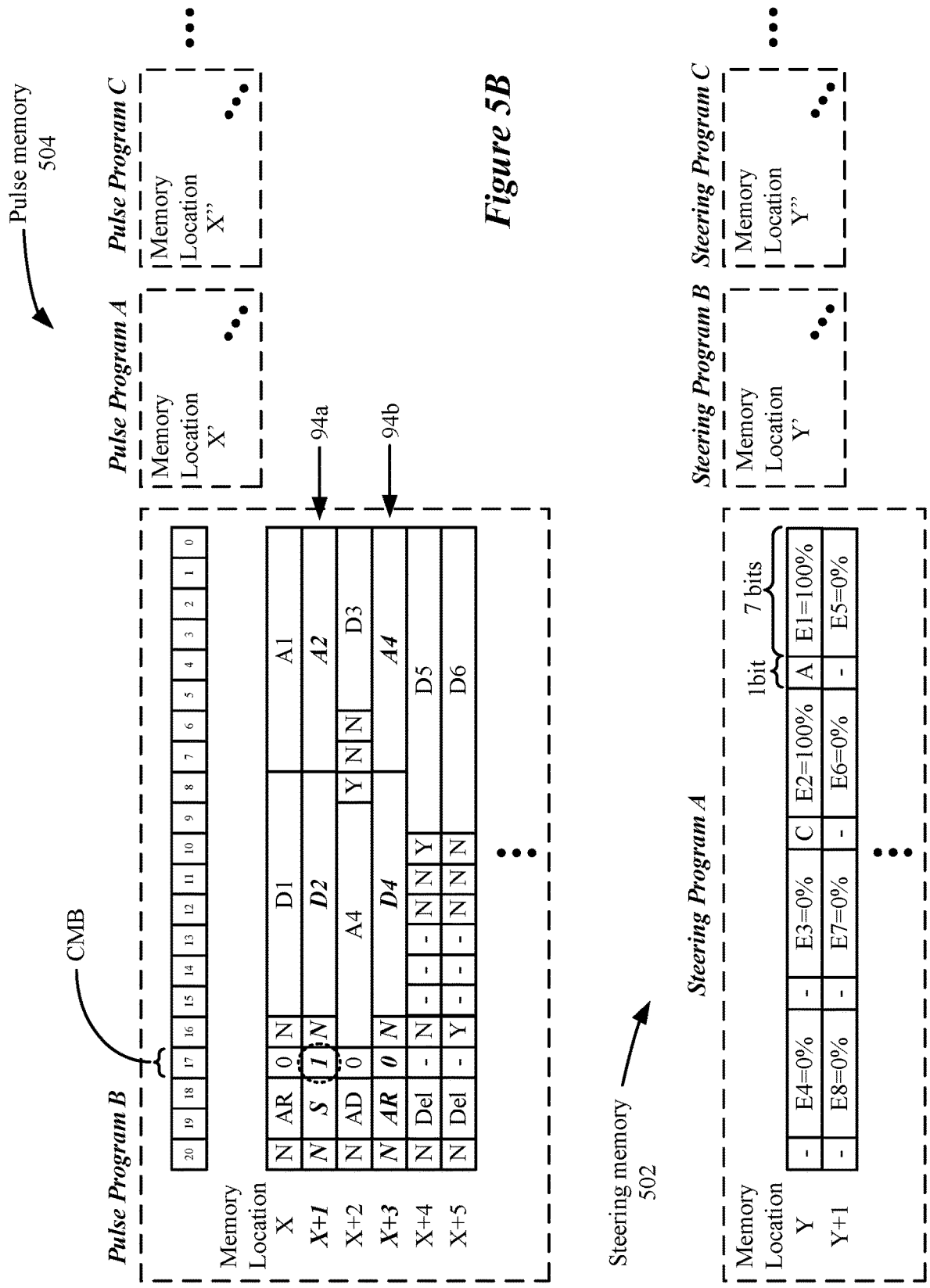

As taught in the above-incorporated '265 patent, the unique configuration of the stimulation circuitry 170 as shown in FIG. 4A allows for the efficient production of stimulation waveforms of unique shapes. FIG. 5A shows an example of a pulse train that can be produced in a particular timing channel (e.g., TC1, using PDAC 171(1) and PDAC1/NDAC1) using this stimulation circuitry. In this example, two electrodes E1 and E2 have been selected for stimulation, which occurs by selection of a particular steering program A in steering memory 502, as shown in FIG. 5B. Steering program A may be stored starting at location Y, with each location storing data for four of the electrodes. One quarter of each location (8 bits) stores the data for a particular electrode, including a bit indicating whether the electrode is to comprise an anode ('1') or cathode ('0'), and up to seven bits indicating a percentage of the anodic or cathodic current that that electrode is to receive. Multiple steering programs can be stored in steering memory 502 (e.g., B starting at memory location Y'; C starting at memory location Y"), each designating a different one or more electrodes to operate as anodes and one or more electrodes to operate as cathodes, and a percentage of the total anodic and cathodic current such electrodes will receive.

Also shown in FIG. 5B are a number of pulse programs stored in pulse memory 504. Pulse programs specify the basic shape of a pulse, including amplitude (A) and duration (D) of its various phases. Example pulse program B is shown as starting at memory location X, with each successive location including data defining the shape of a successive pulse phase. Only 20 of the 32 available bits may be used at each location to define the pulse phases. As explained in the '265 patent, bits 19 and 18 specify a type of pulse phase, which dictates the format of the remaining bits in that memory location. For example, pulse phase types may comprise active stimulation phases specifying a stimulation amplitude and duration, or delay phases (Del) which don't involve stimulation and thus only specify a duration. The reader can refer to the '265 patent for a more complete discussion of the types of pulse phases and the various bits that are stored with each.

Of relevance to the pulse train example depicted in FIG. 5A are the active stimulation phases of a biphasic pulse, which have been bolded at memory locations X+1 and X+3. In particular, note in FIG. 5B pulse phase type 'S' ("stimulation") which prescribes the amplitude (A2) and duration (D2) of the first pulse phase 94a (FIG. 3) of a biphasic pulse, and pulse phase type 'AR' ("active recovery") which prescribes the amplitude (A4) and duration (D4) of the second pulse phase 94b. (If the biphasic pulse is symmetric, note that D2=D4 and A2=A4).

A pulse program is not limited to storing only biphasic pulses. Indeed, pulse phase types can be concatenated in any order to define pulses of non-conventional shapes. For example, although not shown, a pulse program may comprise a number of successive stimulation phases (type 'S') of increasing amplitudes, which would create a pulse with a rising stair-stepped shape. The above-incorporated '265 patent provides still other examples of pulse shapes formable using the disclosed circuitry and software.

Figure 5C:
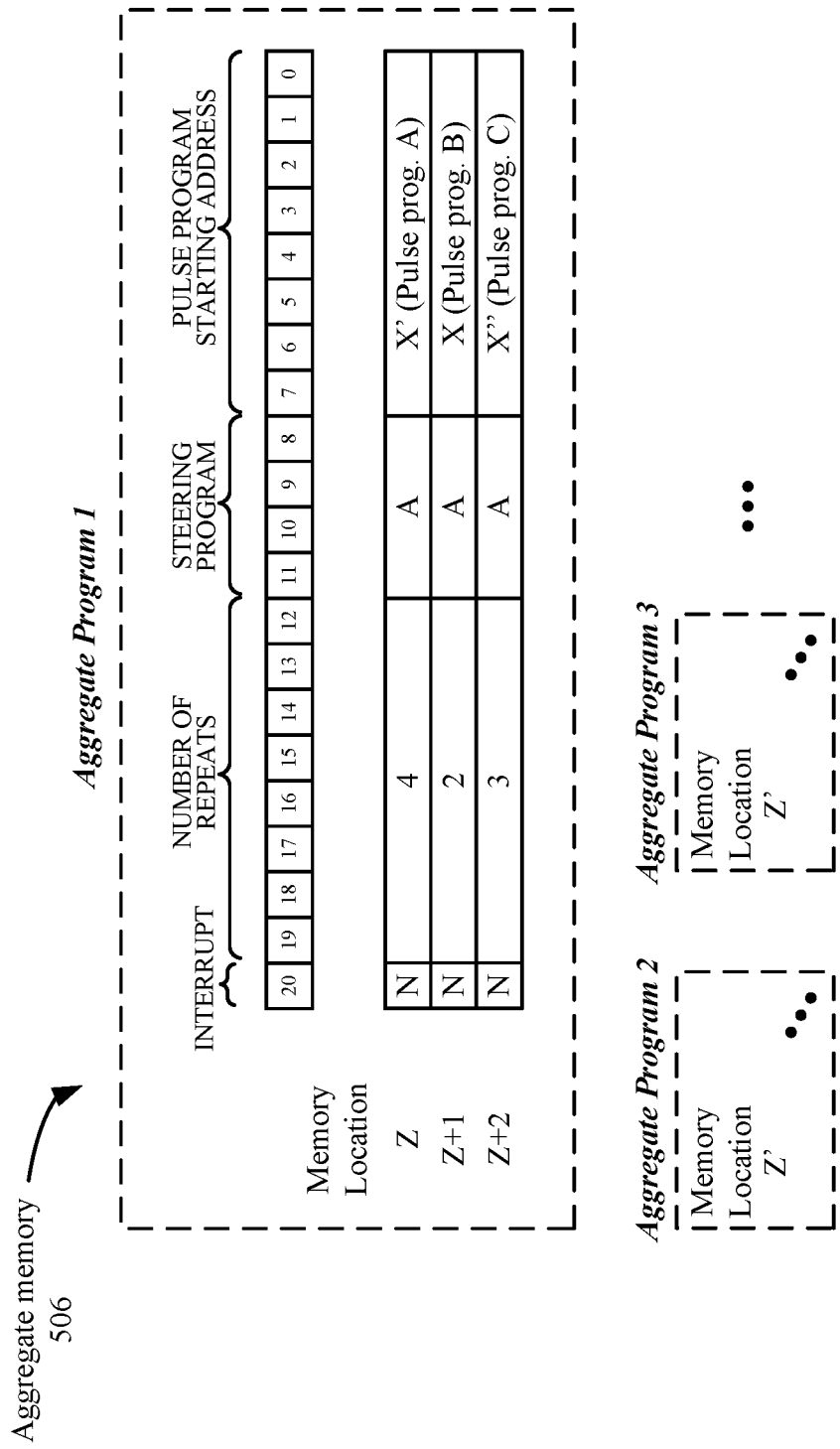

Any pulse program in memory 504 may be associated with any steering program in memory 502 to create pulses defined by the pulse program at the electrodes defined in the steering program, and this occurs by use of an aggregate program stored in aggregate memory 506, as shown in FIG. 5C. Each memory location of the aggregate program is formatted to specify a steering program and the starting address of a pulse program. Further, each location specifies a number of times at which a pulse (including its various phases as specified in the pulse program) will repeat. (An interrupt bit can also be set, which may be used to interrupt the microcontroller 150 for any number of purposes). Successive locations can define other pulse program/steering program associations, and pulse repeat numbers.

FIG. 5A shows the pulse train formed using the aggregate program 1 of FIG. 5C. Three pulse programs A, B, and C are successively specified in the aggregate program, whose pulses are repeated 4, 2, and 3 times respectively. The same steering program A (FIG. 5B) is associated with each pulse program in aggregate program 1, specifying use of electrode E1 and as anode, and E2 as a cathode. Notice that the aggregate program 1 repeats; although not shown, this can be affected by defining the start (Z) and end (Z+2) memory location in the configuration memory 508 (FIG. 4A).

While stimulation circuitry 170 and DAC circuitry 172 are beneficial in their ability to efficiently form and concatenate stimulation pulses of different shapes, the inventors realize that such flexibility gives rise to new challenges, in particular as concerns management of the compliance voltage, VH. As discussed earlier, adjustment of the compliance voltage VH is desirable to ensure that stimulation pulses can be reliably formed without wasting power (the battery 14) in the IPG 10.

But compliance voltage management is made difficult when the amplitude of pulses can be quickly and significantly altered, as occurs in the example of FIG. 5A. Compliance voltage measurements—such as the voltage drops across the PDAC (Vp) and NDAC (Vn) (FIG. 3)—could be taken during every stimulation pulse. But this would be difficult to manage and implement. For example, suppose measurements taken during pulse program A—when the pulse amplitudes are low—indicate that the compliance voltage VH is not too high or too low. When the first high-amplitude stimulation pulse of pulse program B issues, the compliance voltage may likely be too low, and therefore pulse program B's pulses may not issue with the prescribed amplitudes. In short, the therapy specified by the aggregate program 1 may not be reliably issued to the patient.

Figure 5D:
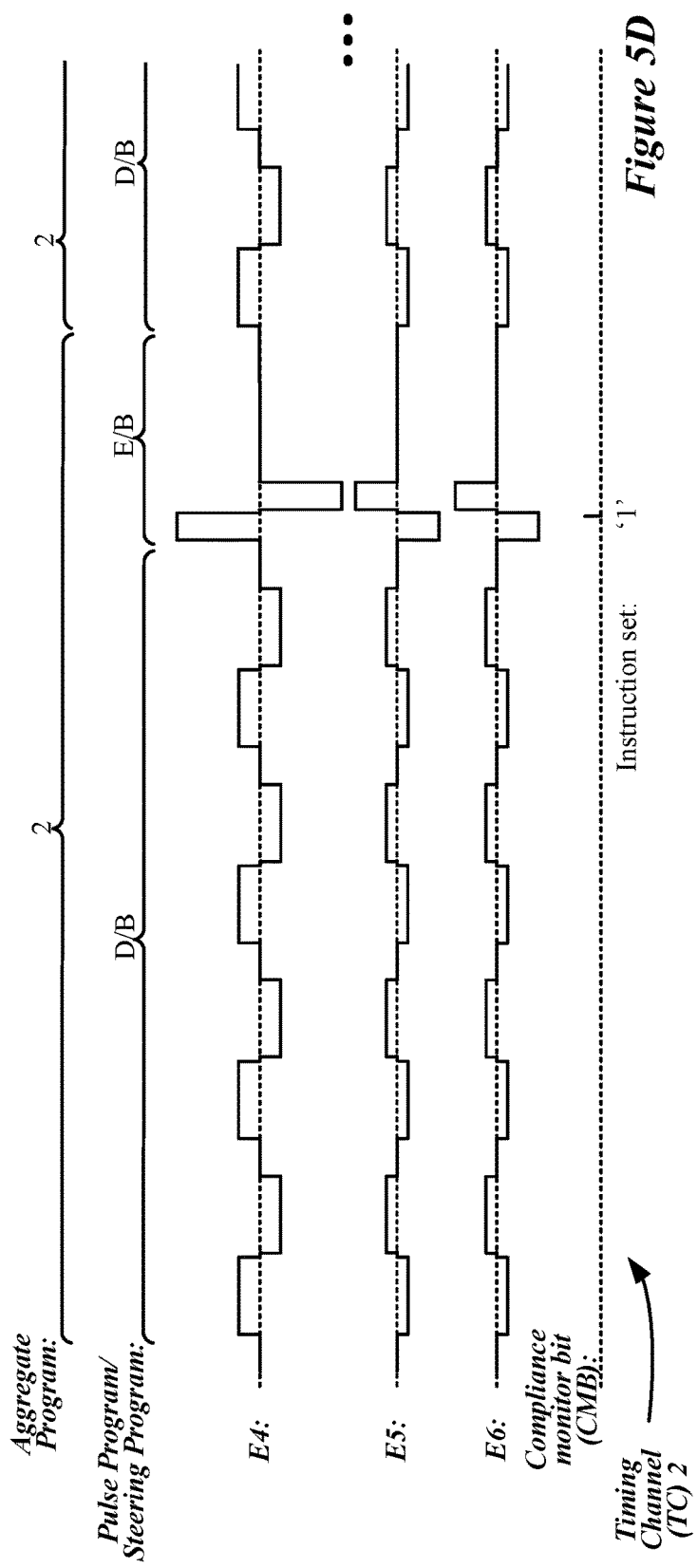
FIG. 5D shows a different pulse train issued according to a second aggregate program in a second timing channel. In both aggregate programs, a compliance monitoring bit is set to enable a compliance voltage measurement during some of the pulses.

This problem is exacerbated when it is realized that stimulation circuitry 170 and DAC circuitry 172 support the concurrent execution of stimulation pulses in different timing channels. For example, FIG. 5D shows another example of a pulse train being issued in a second timing channel (TC2) on electrodes E4, E5, and E6 as defined by a steering program B. Different pulse programs D and E are also used, which are associated with steering program B in an aggregate program 2. Like timing channel 1 (FIG. 5A), the pulses in timing channel 2 vary significantly in amplitude, with pulse program E defining a pulse of a particularly high amplitude, which aggregate program 2 repeats only once. Because timing channels 1 and 2 run concurrently, it is not a simple matter to decide when to make measurements relevant to adjusting the compliance voltage, or how such measurements should be used to set the compliance voltage.

The inventors address this issue by providing in software the ability to specify which stimulation pulses are to be measured as relevant to monitoring and adjusting the compliance voltage. Preferably, specifying such pulses occurs by setting a compliance monitor bit in the program that defines the pulse, and more particularly the compliance monitor bit may be set at a memory location defining a particular pulse phase during which the compliance voltage should be monitored. When a compliance monitor bit is issued, the active electrode node voltages are monitored and compared to desired ranges to determine whether they are high or low. Compliance logic operates on these high/low signals and processes them to decide whether to issue a compliance voltage interrupt to the microcontroller, which can then instruct the compliance voltage generator to increase or decrease the compliance voltage.

Defining in software which pulses (or more generally, pulse phases) are to be measured as relevant to compliance voltage monitoring and adjustment preferably occurs by inclusion of compliance voltage monitoring data, which may comprise a single compliance monitoring bit (CMB), although longer data structures could be used as well. As shown in FIG. 5B, and preferably, such compliance monitor bit may be defined in the format of certain pulse phase types in a pulse program. For example, bit 17 comprises a compliance monitor bit in certain active and delay pulse phase types, thus allowing compliance measurements to be taken during such pulse phases if desired.

The compliance monitoring bit can be set with an instruction or not, and as explained further below, the instruction is configured to instruct the compliance circuitry to process the voltages at the selected electrode nodes during the relevant pulse phase with which the instruction is stored. Compliance monitoring bit instructions are preferably in a fashion sensible for compliance voltage control. For example, in the example timing channel TC1 of FIG. 5A, notice that the compliance monitoring bit has only been set with an instruction (a logic state '1') for the high amplitude pulses used in pulse program B, but has not been set with an instruction (logic state '0') not for the smaller pulses in pulse programs A and C. Specifically, the compliance monitoring bit is set only during the first pulse phase 94a of the pulses in pulse program B, which bit is circled in FIG. 5B.

The disclosed architecture also allows the timing of the issuance of the compliance monitoring bit instruction to be defined, which is important because the issuance of this bit sets the timing at which measurements relevant to the compliance voltage are made. The timing of the compliance monitoring bit instruction is shown in the magnified view at the bottom right of FIG. 5A, which timing in this example is set using the configuration memory 508 (FIG. 4A). Within this memory 508 is a compliance monitor timing register 509, which defines when the compliance monitoring bit instruction will issue during the duration of the pulse phase in which it is set. Such timing may be defined in a number of ways. For example, the compliance monitor timing register 509 may specify a percentage during the duration (e.g., D2) of the pulse phase during which the compliance monitoring bit instruction issues, with 1% specifying issuance of the bit at the beginning of the duration, and 99% specifying issuance at the end of the duration. Alternatively, register 509 can store a time offset (e.g., 1 μs) from either the beginning or end of the pulse phase at which the CMB instruction will issue. Such time offset can be quantified by other measures of time, such as a number of cycles of a clock operating with the ASIC 160. Compliance monitor bit instruction timing could also occur after the pulse phase in other examples.

It is preferred to set the timing of the issuance of the compliance monitoring bit instruction to when the compliance voltage VH is most likely to be inadequate. In the example shown in FIG. 5A, this occurs just before the end of the first pulse phase 94a. This is the worst case for a biphasic pulses: at the end of the first pulse phase, the DC-blocking capacitors 55 (FIG. 3) will be charged to their maximum extent, and thus the voltage across them (VC1, VC2) will be at their highest. This minimizes the voltage drops across the PDAC and NDAC (Vp, Vn) for the same compliance voltage, VH, meaning that the PDAC and NDAC are at risk for having too little power to produce pulses of prescribed amplitudes. In other words, VH is mostly likely too low at this point, and hence it is important to take a compliance voltage measurement at this point to verify compliance voltage adequacy.

To summarize, compliance voltage measurements are preferably taken at times during the first timing channel TC1 when the compliance voltage VH might be expected to be most inadequate. This allows the compliance voltage to be set at a level that is high enough to reliably form the high amplitude pulses (during pulse program B). Smaller amplitude pulses (during pulse programs A and C) can be ignored during compliance monitoring (the CBM bits are not set to '0', and hence no compliance monitoring instruction). The established compliance voltage will be higher than necessary to form these smaller pulses. This wastes power in the creation of these smaller pulses, but is a reasonable trade off, as it ensures that an adequate compliance voltage will be formed for all pulses, and that minimal compliance measurements and adjustment will need to be made.

Notice that timing channel TC2 of FIG. 5D has similarly defined issuance of a compliance monitoring bit instruction during the high amplitude pulse used in pulse program E, but not for the smaller pulses in pulse programs D. This is logical for the same reasons just discussed for timing channel TC1. As will be seen in further detail with respect to FIG. 6D, compliance voltage measurements can be taken during pulses (or pulse phases) in both timing channels 1 and 2. This ensures that measurements are made will be adequate to adjust the compliance voltage to be sufficient for all pulses in all timing channels. However, it isn't strictly necessary to set compliance monitor bits with instruction in pulses in all active timing channels.

Compliance monitoring instructions can be set in different ways. For example, compliance monitor bits could be set to '1' by a user writing the pulse program or the aggregate program which calls it to provide therapy to a patient. This would most likely be done with the assistance of an external clinician programmer computer system, which would allow the clinician to set the compliance monitor bits (and/or write the pulse and aggregate programs), and wirelessly transmit the program(s) to the memory circuitry in the IPG 10. See, e.g., U.S. Patent Application Publication 2015/0360038 (disclosing a clinician programmer for setting or adjusting a patient's stimulation therapy). A compliance monitor bit may also be set automatically by the IPG 10 or the external programmer software. For example, the IPG 10 (e.g., aggregate logic 516; FIG. 4A) may realize that a particular aggregate program has certain particularly high amplitude pulses, and may set the compliance monitor bit with instructions for those pulses. In this regard, note that the compliance monitoring instructions can be defined in data structures other than the pulse programs depicted in FIG. 5B.

Figure 6A:
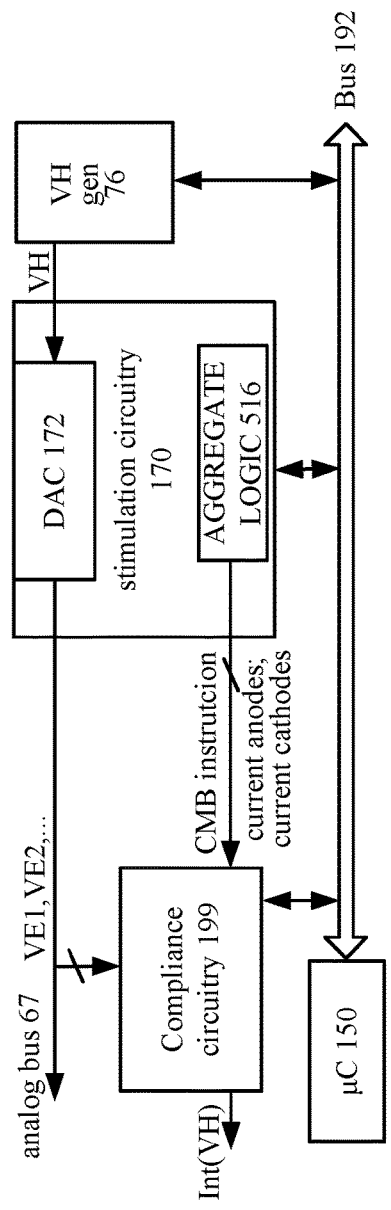
FIG. 6A shows inclusion of a compliance detector within the ASIC 160.

FIG. 6A shows further details concerning integration of compliance voltage monitoring and adjustment in ASIC 160. As shown, the voltage at the electrodes nodes 61a (VE1, VE2, etc.) are reported along analog bus 67 from the DAC circuitry 172 to compliance circuitry 199, which in one example comprises a compliance detector 201 and compliance logic 220, as depicted in further detail with respect to FIGS. 6B-6D. Circuitry 199 also receives the compliance monitor bits instructions with the appropriate timing when issued from the aggregate logic 516 that is executing an aggregate program, hence providing stimulation pulses to the patient. Aggregate logic 516 further provides to compliance circuitry 199 information regarding which electrodes are currently—during the pulse phase in which the compliance monitor bit is specified—acting as anodes and cathodes. This allows the circuitry 199 to understand which electrode node voltages are relevant to monitor when a compliance monitoring bit instruction issues, as explained further below. If compliance circuitry 199 determines from the compliance voltage measurements that the compliance voltage VH is too high or too low, it can issue a compliance voltage interrupt (Int(VH)) to the microcontroller block 150, which can in turn take certain actions as discussed in further detail with respect to FIGS. 7A-7C. Note that interrupt Int(VH) can be communicated to the microcontroller block 150 either via the internal bus 192, or directly and independently of the bus.

Figure 3:
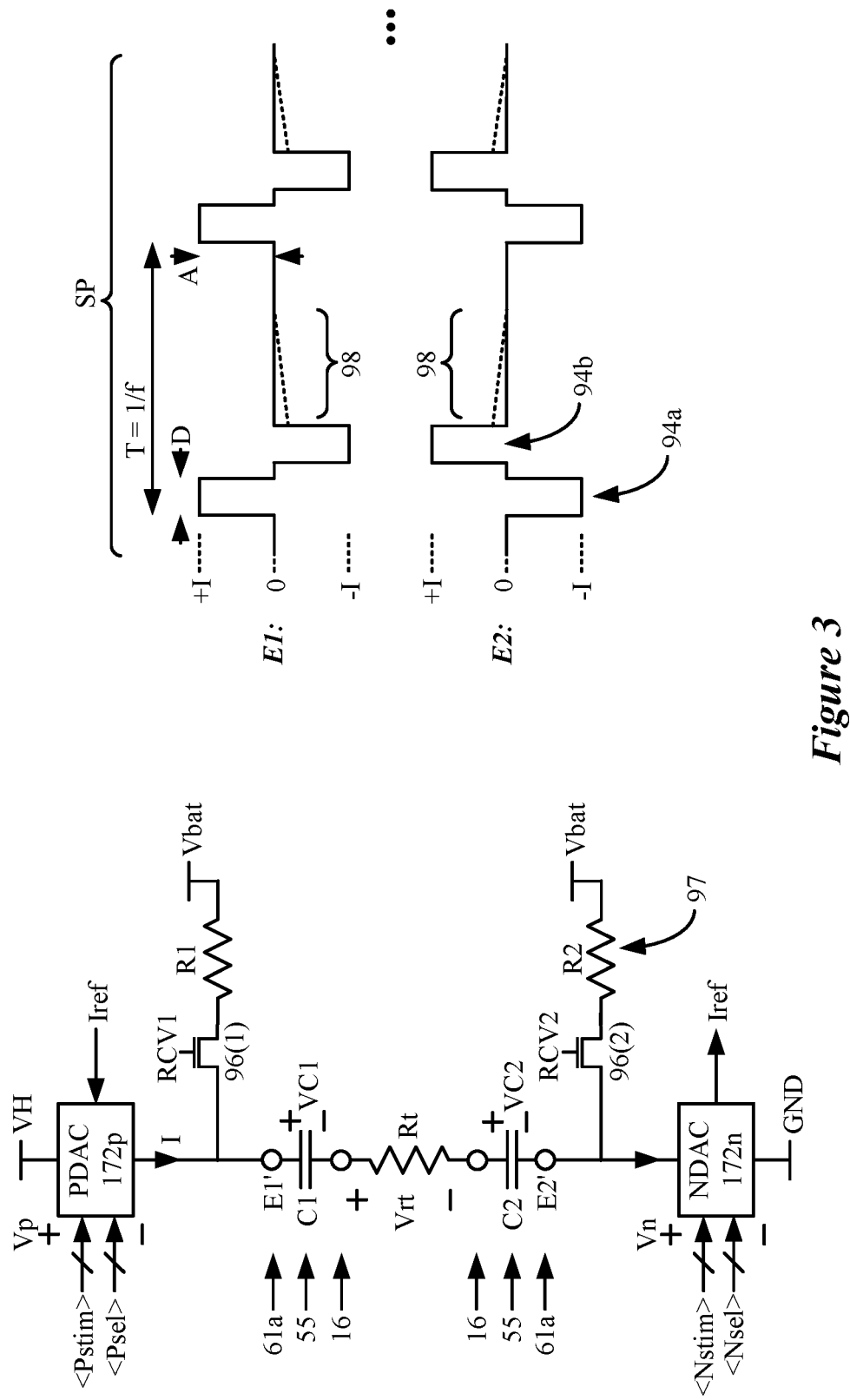
FIG. 3 shows aspects of the Digital-to-Analog Converters (DACs) within the stimulation circuitry of the ASIC, and stimulation pulses formable thereby.
Figure 6B:
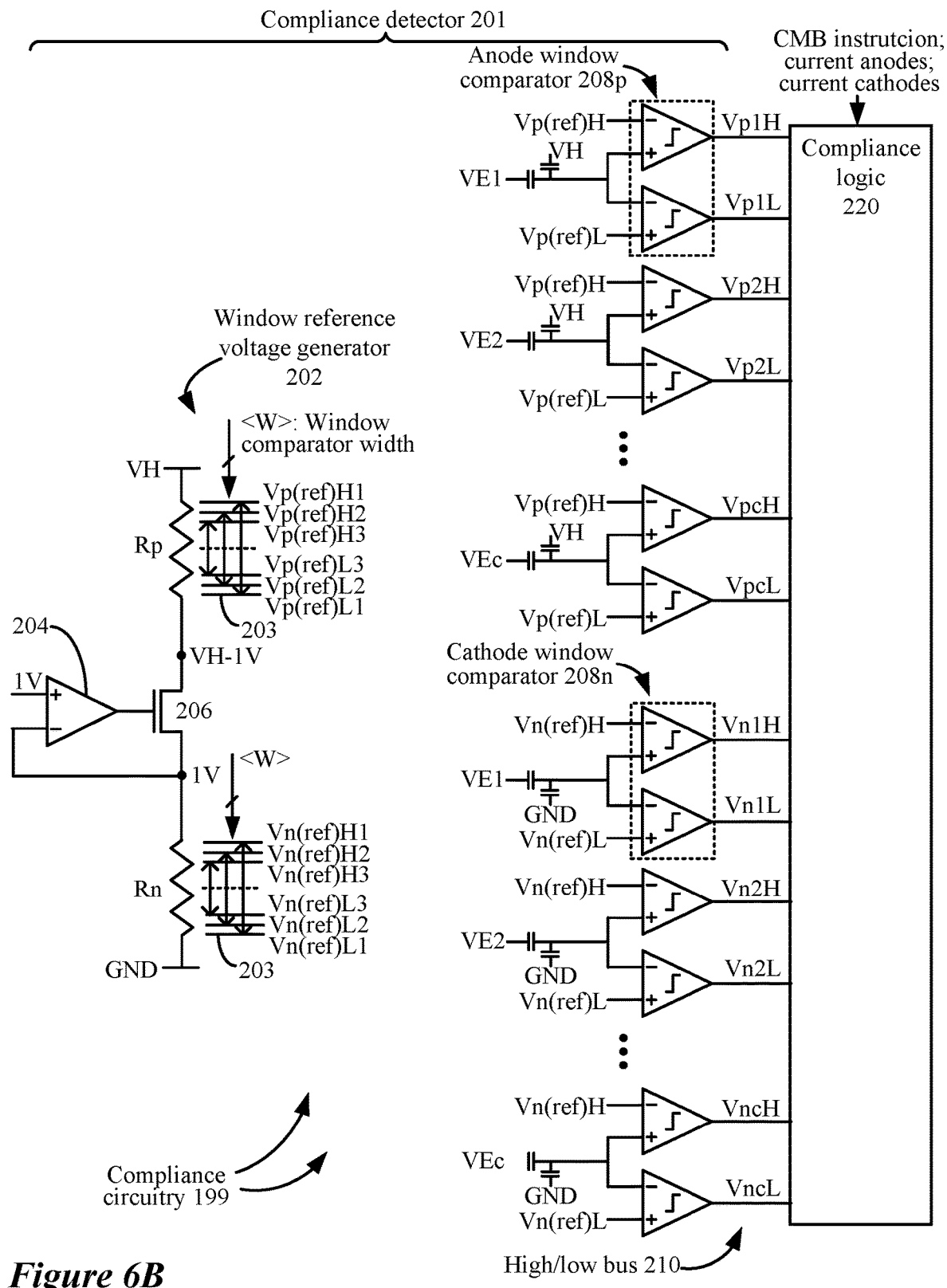
FIGS. 6B-6D show details of the compliance detector.

FIG. 6B shows further details of the compliance detector 201 within compliance circuitry 199. The compliance detector 201 effectively determines the voltage drops across the active PDAC and NDAC circuitry, akin to Vp and Vn as shown in FIG. 3, although such voltage drops may not be directly measured by compliance detector circuitry 201 (although they could be). Instead, and as shown below, these voltage drops are inferred by assessing the voltages at the active electrode nodes 61a, VEx, and scaling their values to appropriate levels for comparison to various reference values to determine whether they are high or low—and hence whether the voltage drops across the PDACs or NDACs are high or low.

Compliance detector 201 receives the electrode node voltages and inputs each into an anode window comparator 208p and a cathode window comparator 208n. Anode window comparators 208p receive anode high and low reference voltages, Vp(ref)H and Vp(ref)L, between which is a desired range for the input electrode node voltages when they are operating as anodes. If an anode electrode node voltage (e.g., VE1) is too high (>Vp(ref)H), the anode window comparator 208p will output an anode high signal (e.g., Vp1H='1') to compliance logic circuitry 220, described in further detail with respect to FIG. 6C. If an anode electrode node voltage is too low (<Vp(ref)L), the anode window comparator 208p will output an anode low signal (e.g., Vp1L='1') to compliance logic circuitry 220. Cathode window comparators 208n receive cathode high and low reference voltages, Vn(ref)H and Vn(ref)L, between which is a desired range for the input electrode node voltages when they are operating as cathodes. If a cathode electrode node voltage (e.g., VE1) is too high (>Vn(ref)H), the cathode window comparator 208n will output a cathode high signal (e.g., Vn1H='1'), or if too low (<Vn(ref)L), the cathode window comparator 208n will output a cathode low signal (e.g., Vn1L='1').

Thus, the window comparators 208 can establish four digital signals (e.g., Vp1H, Vp1L, Vn1H, Vn1L) for each electrode node voltage (e.g., VE1), depending whether that electrode is operating as an anode or cathode, and whether the voltage is too high or too low. Together, these four signals for all of the electrodes comprise a high/low bus 210 received by the compliance logic 220.

The anode and cathode high and low reference voltages are formed by a window reference voltage generator 202. Generator 202 comprises an op amp 204, which receives a reference voltage, such as a 1V. Op amp 204 outputs to a transistor 206 which is serially connected by an upper resistor Rp to the compliance voltage VH, and by a lower resistor Rn to ground. Feedback establishes the reference voltage (1V) across the lower resistor, Rn, and because Rp=Rn, the reference voltage is also dropped across the upper resistor Rp. The upper and lower resistors Rp and Rn comprise a number of taps 203, which taps can be selected to operate as the reference voltages used by the window comparators 208p and 208n. More specifically, window comparator width control signals <W> choose a pair of anode reference voltages and a pair of cathode reference voltages. The pair chosen establishes a smaller or larger desired range of acceptable voltages for the input electrode nodes at the window comparators. For example, if Vp(ref)H3/L3 and Vn(ref)H3/L3 are chosen, the windows are relatively small; therefore, VpxH and VpxL and VnxH and VnxL are more likely to be asserted by the window comparators. By contrast, if Vp(ref)H1/L1 and Vn(ref)H1/L1 are chosen, the windows are relatively big; therefore, VpxH and VpxL and VnxH and VnxL are less likely to be asserted by the window comparators. Why it may be warranted to vary the window comparator width via control signals <W> is discussed further below.

The anode and cathode high and low reference voltages are preferably symmetric with respect to VH and the reference voltage. For example, if Vn(ref)H2=0.6V and Vn(ref)L2=0.4V, then Vp(ref)H2 is preferably VH −0.4V and Vp(ref)L2 is preferably VH −0.6 V.

The electrode node voltages VEx are preferably adjusted by capacitors before being provided to the inputs of the individual comparators in each window comparator. At the anode window comparators 208p, the capacitors reference the electrode voltages to the compliance voltage, VH, thus making this input to the comparators depend on VH, which can vary. This is important, because the anode high and low reference voltages provided by the generator 202 to the anode window comparators 208p are also dependent on VH. VH variation is less important as concerns the cathode window comparators 208n, because the cathode high and low reference voltages provided by the generator 202 are held steady by the reference voltage (e.g., 1V). Nonetheless, symmetrical referencing of the electrode node voltages to ground by the capacitors ensures that the voltage inputs into the comparators are of the right magnitude compared to the cathode high and low reference voltages. Resistors could be used as well as capacitors to adjust the values of the electrode node voltages.

Figure 6C:
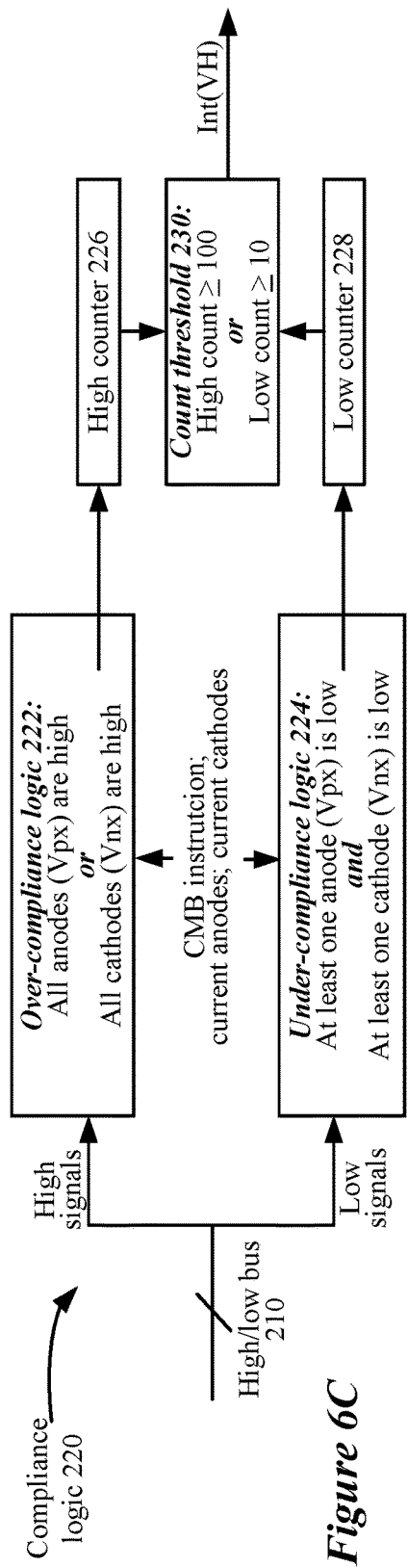

As shown in FIGS. 6B and 6C, the compliance logic 220 receives the compliance monitor bits instructions when issued, and further receives information regarding which electrodes are currently acting as anodes and cathodes. This allows compliance logic 220 to know when to sample the signals on the high/low bus 210, and which of those signals are relevant at any given time.

The compliance logic 220 is shown in detail in FIG. 6C, and as just mentioned, it receives the signals on the high/low bus 210 indicating whether particular electrode node voltages are high, low, or neither at the moment. Essentially, the compliance logic 220 employs an algorithm to decide when the compliance voltage, VH, may need adjustment, and issues interrupt Int(VH) to the microcontroller 150 as stated above. As discussed in detail below, the compliance logic's algorithm employs sophistication to issue the interrupt sensibly, and preferably doesn't issue the interrupt whenever a single high or low signal is issued on the high/low bus 210.

As FIG. 6C shows, the high/low signals on bus 210 are processed by two different logic blocks: an over-compliance logic block 222 and an under-compliance logic block 224. When a compliance monitor bit (CMB) instruction issues, logic blocks 222 and 224 sample the high/low signals corresponding to the currently active anodes and cathodes, and employ rules to decide whether to increments counters 226 and 228. If all anodes are high, or if all cathodes are high, then the over-compliance logic block 222 increments a high counter 226. By contrast, if at least one anode is low and at least one cathode is low, then the under-compliance logic block 224 increments a low counter 228. The rationale for the rules employed by the logic blocks 222 and 224 relate to the interdependence of the PDAC and NDAC circuitry in forming pulses. In any event, other rules could operate within the logic blocks 222 and 224.

Figure 6D:
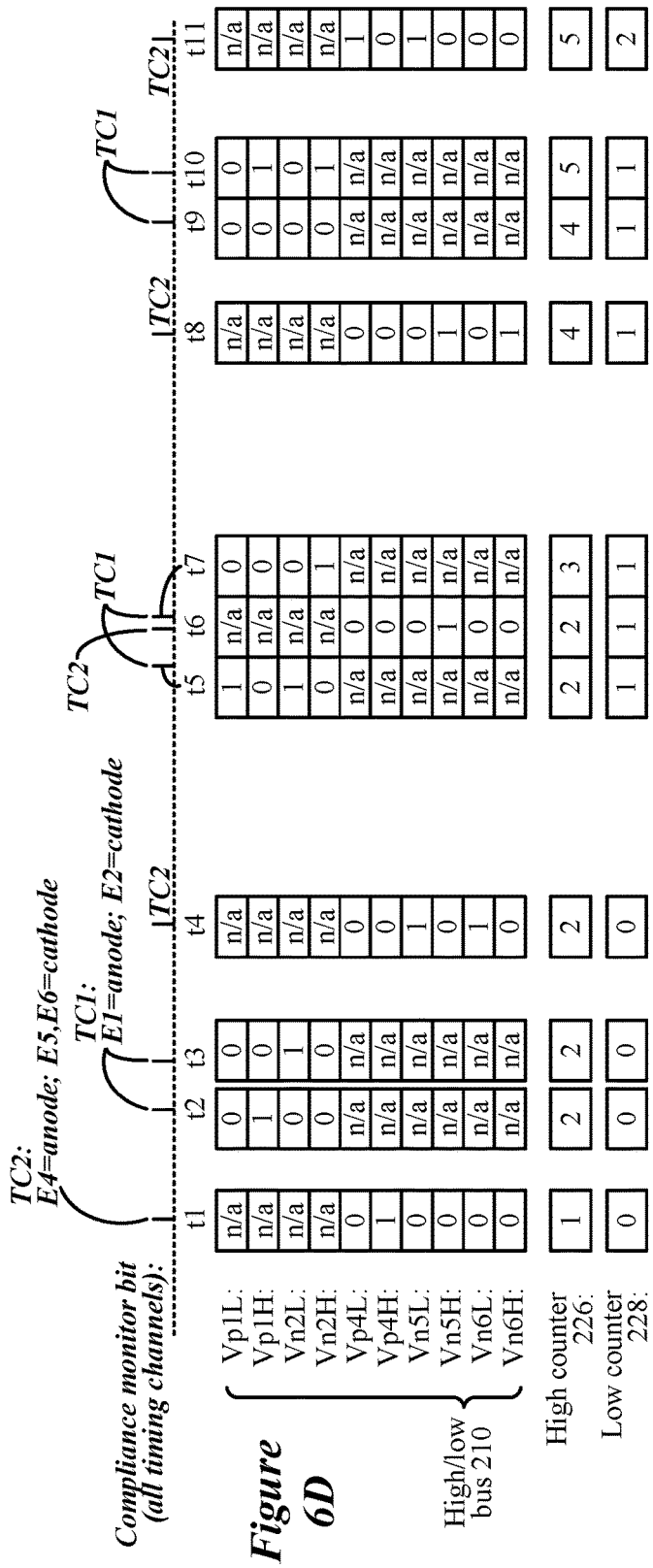

FIG. 6D shows an example explaining operation of the logic blocks 224 and 224 and counters 226 and 228. Compliance monitoring bits are issued at times t1-t11, and generally correspond to the compliance monitor bits established in timing channels 1 (TC1; FIG. 5A) and 2 (TC2; FIG. 5D) illustrated earlier. The table shows relevant high/low signals from bus 210. Because TC1 only involves electrode node E1 as an anode and E2 as a cathode, only high/low signals Vp1H, Vp1L, Vn2H, and Vn2L are relevant and considered by the logic blocks 222 and 224 when CMB instructions issue in TC1. Because TC2 only involves electrode node E4 as an anode and E5 and E6 as cathodes, only high/low signals Vp4H, Vp4L, Vn5H, Vn5L, Vn6H, and Vn6L are relevant and considered by the logic blocks 222 and 224 when CMB instructions issue in TC2. As mentioned above, aggregate logic 516 can inform compliance logic 220, and blocks 222 and 224 in particular, which electrode node voltages are current active as anodes and cathodes.

At time t1, a CMB instruction issues in TC2, and the voltage at anode E4 is high (Vp4H='1'). E4 is the only anode active at the time, and hence all anodes are high, meeting over-compliance block 222's rule, and thus incrementing high counter 226.

At time t2, a CMB instruction issues in TC1, and the voltage at anode E1 is high (Vp1H='1'). E1 is the only anode active at the time, and hence all anodes are high, meeting over-compliance block 222's rule, and thus incrementing high counter 226 again.

At time t3, a CMB instruction issues in TC1, and the voltage at cathode E2 is low (Vn2L='1'). But no anodes (E1) are low. This does not meet under-compliance block 224's rule, and thus low counter 228 is not incremented.

At time t4, a CMB instruction issues in TC2, and the voltage at cathodes E5 and E6 are low (Vn5L=Vn6L='1'). But no anodes (E4) are low. This does not meet under-compliance block 224's rule, and thus low counter 228 is not incremented.

At time t5, a CMB instruction issues in TC1, and the voltage at anode E1 is low (Vp1L='1') and the voltage at cathode E2 is low (Vn2L='1'). This meets under-compliance block 224's rule, and thus low counter 228 is incremented.

At time t6, a CMB instruction issues in TC2, and the voltage at cathode E5 is high (Vn5H='1'). There is however another cathode E6, and it is not high. This does not meet over-compliance block 222's rule, and thus high counter 226 is not incremented.

At time t7, a CMB instruction issues in TC1, and the voltage at cathode E2 is high (Vn2H='1'). E2 is the only cathode active at the time, and hence all cathodes are high, meeting over-compliance block 222's rule, and thus incrementing high counter 226.

At time t8, a CMB instruction issues in TC2, and the voltage at cathodes E5 and E6 are high (Vn5H=Vn6H='1'). These are all of the active cathodes, meeting over-compliance block 222's rule, and thus incrementing high counter 226.

At time t9, a CMB instruction issues in TC1, and the voltages at anode E1 and cathode E2 are neither high nor low (all='0'). Hence, neither block 222 nor block 224's rules are met, and neither of counters 226 and 228 are incremented.

At time t10, a CMB instruction issues in TC1, and the voltages at anode E1 and cathode E2 are high (Vp1H=V2nH='1'). This meets over-compliance block 222's rule (for two reasons), and thus high counter 226 is incremented.

At time t11, a CMB instruction issues in TC2, and the voltage at sole anode E4 is low (Vp4L='1'), and the voltages at cathode E5 is low (Vn5L='1'). This meets under-compliance block 224's rule, even though additional cathode E6 is not low. Hence, low counter 228 is incremented.

FIG. 6D doesn't likely represent an actual use, because an IPG 10 would not ordinarily experience such frequent changes in the high/low signals on bus 210. Nonetheless, FIG. 6D does show how various combinations of high/low signals would be processed by the compliance logic 220.

Returning to FIG. 6C, the counts accumulating in the counters 226 and 228 are reported to a count threshold logic block 230. In block 230, the count in either of the counters 226 and 228 must meet or exceed a threshold value before the compliance logic 220 will issue the interrupt Int(VH) to the microcontroller 150. This is desired to keep from needlessly over-correcting the compliance voltage. It would be expected during operation of the IPG that some pulses will from time to time not issue perfectly due to noise or other factors. Such spurious occasions preferably should not by themselves give rise to an interrupt, even if they meet the rules of over- and under-compliance logic blocks 222 and 224 and cause high or low counters 226 or 228 to increment. Instead, a number of high or low counts is required to ensure that the compliance voltage is truly too high or too low, and therefore that it is worthwhile to interrupt the microcontroller 150 so that it may take action, as described subsequently.

In count threshold logic block 230, the high count threshold and the low count threshold need not be equal. Instead, in one example, the high count threshold is set to 100, meaning that the high counter 226 must equal 100 or greater before the interrupt Int(VH) is issued; whereas the low count threshold is set to 10, meaning that the low counter 228 must equal 10 or greater before the interrupt Int(VH) is issued. This difference in high and low thresholds is preferred because a compliance voltage that is too high may be considered less problematic than a compliance voltage that is too low: if the compliance voltage is too high, power may be wasted, but stimulation pulses will still be reliably issued; if the compliance voltage is too low, at least some stimulation pulses may be issued with amplitudes that are too small, hence affecting therapy. Having said this, a single threshold value in other designs could be used and applied to both high and low counts.

If the compliance logic 220 has a count that exceeds a threshold—whether high or low—the interrupt Int(VH) issues as mentioned previously. It is worth noting that to this point the disclosed technique for monitoring the compliance voltage doesn't require any assistance from the microcontroller 150. The CMB instructions are set in the memory in the stimulation circuitry 170 and automatically issued to the compliance logic 220; and the compliance detector 201 and compliance logic 220 can otherwise operate by themselves without microcontroller 150 assistance. This offloading of functionality from the microcontroller 150 simplifies system management. Further, this technique is considerate of IPG 10 power, because—from the standpoint of compliance voltage management—the microcontroller 150 is only awoken to take action when it receives an interrupt; the microcontroller 150 may otherwise remain in a low-power sleep state.

Figure 2A:
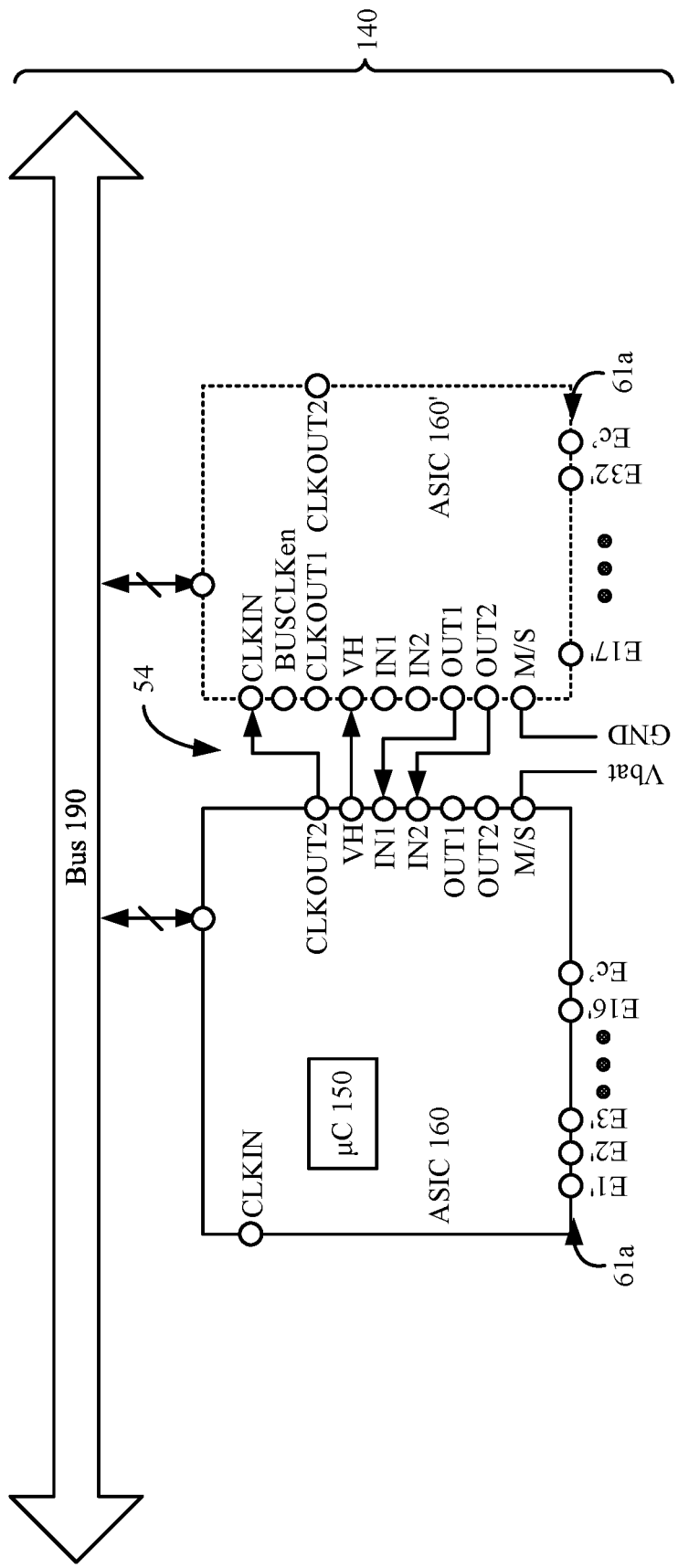
FIG. 2A shows an architecture for an IPG utilizing at least one Application Specific Integrated Circuit (ASIC)
Figure 2B:
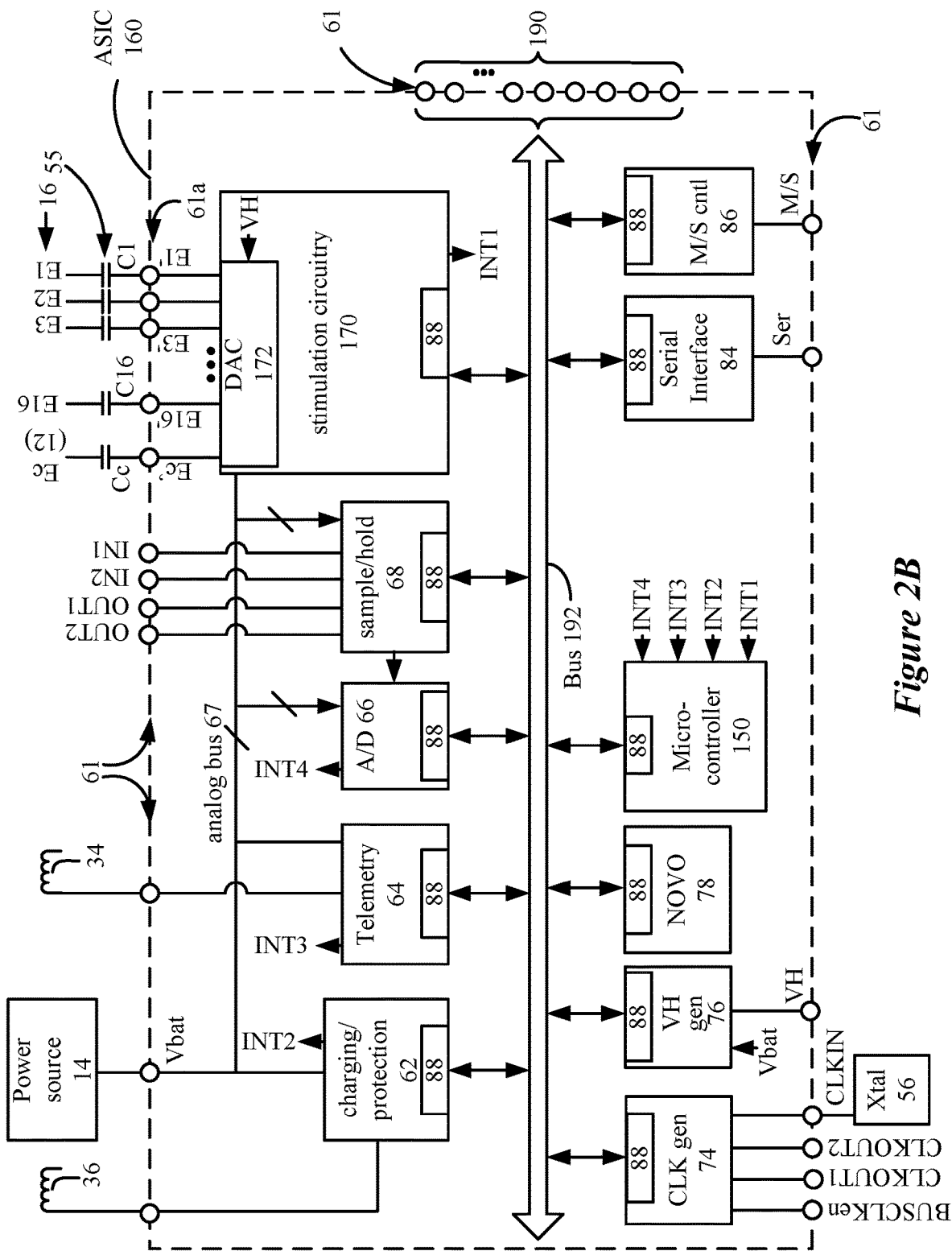
FIG. 2B shows circuitry blocks within the ASIC and connection to off-chip components.
Figure 7B:
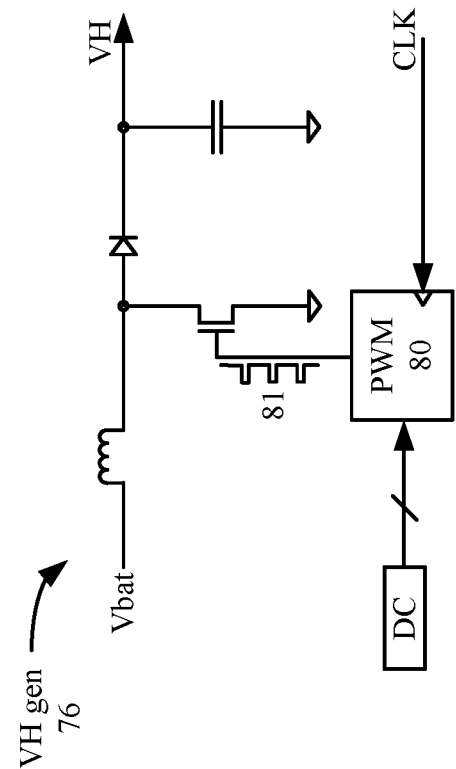
FIGS. 7B and 7C show adjustment of different types of compliance voltage generators.
Figure 7A:
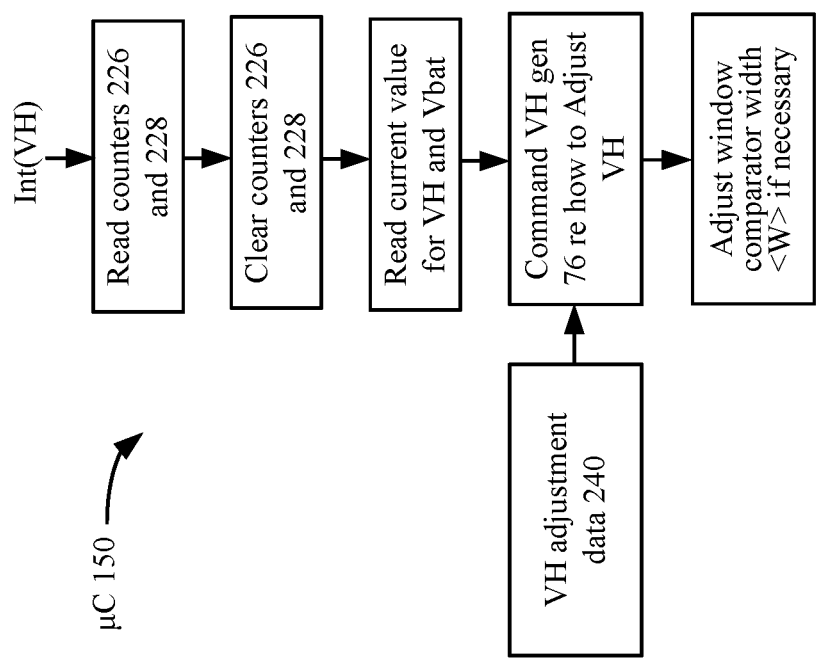
FIG. 7A shows operation of the microcontroller within the ASIC upon receiving an interrupt from the compliance detector to adjust the compliance voltage.

FIG. 7A shows actions the microcontroller 150 can take when it receives the compliance voltage interrupt Int(VH) from the compliance logic 220. First, the microcontroller 150 can read the high counter 226 and low counter 228 via bus 192, and can clear those registers back to a zero count. This is useful so that the microcontroller 150 can understand whether it was interrupted because of an over- or under-compliance voltage condition. However, reading the counters is not strictly necessary. For example, count threshold block 230 could in another example issue two interrupts—Int(VH)H if the high counter 226 is above its count threshold, and Int(VH)L if the low counter 228 is above its count threshold. In other words, the microcontroller 150 may receive a high interrupt and a low interrupt, and so can understand whether the compliance voltage is high or low without having to read any data from the compliance circuitry 199 220. Next, the microcontroller 150 can read the current value for the compliance voltage, VH, and the battery voltage, Vbat, if it's not already known to it. This can occur by reading VH and Vbat from the A/D block (FIG. 2B).

Thereafter, the microcontroller 150 can command the VH generator 76 (FIG. 2B) as to how to adjust the compliance voltage VH it generates. Such command may be relatively simple: for example, if the compliance voltage is too low (as evidenced by low counter 228), the microcontroller 150 can command the VH generator 76 to increase the compliance voltage, perhaps by some set minimal amount or increment (e.g., 0.5V); if the compliance voltage is too high (as evidenced by high counter 226), the microcontroller 150 can command the VH generator 76 to decrease the compliance voltage, again perhaps by some set amount or increment. The compliance voltage monitoring functions described above can continue to run to verify the effectiveness of the compliance voltage adjustment, and the process may be repeated if the compliance voltage needs further adjustment.

Figure 7C:
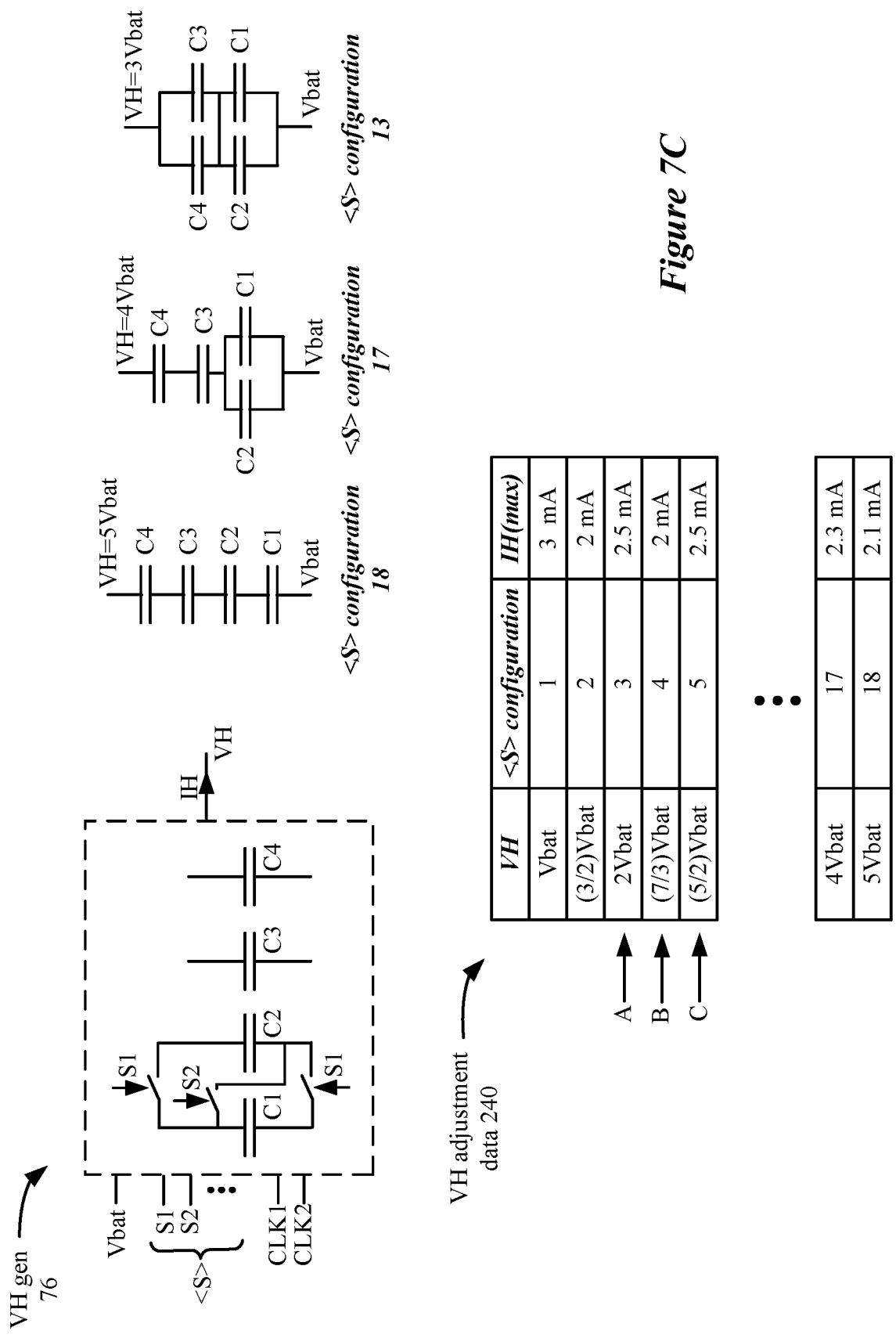

Still referring to FIG. 7A, adjustment to the VH generator 76 may be assisted through the use of VH adjustment data 240, which is preferably stored with the microcontroller 150. Such VH adjustment data 240 may depend on the way the VH generator 76 is built, and two different ways are illustrated in FIGS. 7B and 7C. In FIG. 7B, the VH generator 76 comprises an inductor-based boost circuit, which as is known boosts the battery voltage Vbat to the compliance voltage VH using a pulse width modulator 80 to vary the duty cycle (DC) of a gating signal 81 that controls the converter. Increasing the duty cycle—i.e., the amount of time that the gating signal 81 is on relative to its period—generally increases the compliance voltage VH. See, e.g., U.S. Patent Application Publication 2015/0134029 (discussing boost converter circuitry in further detail). Accordingly, VH adjustment data 240 may not be needed in this design, as the microcontroller 150 can merely command the VH generator 76 to increase or decrease its duty cycle depending whether VH should be increased or decreased.

In FIG. 7C, the VH generator 76 comprises a capacitor-based charge pump. See e.g., U.S. Pat. Nos. 8,219,196; 9,233,254; 7,805,189. In this example, the VH generator 76 comprises a number of capacitors (e.g., C1-C4) that can be charged to the battery voltage, Vbat, during a first clock (CLK1), and then connected together during a second clock cycle in various manners to form various compliance voltages values. The capacitors are connectable by various switches controlled by switch control signals <S> (e.g., S 1, S2, etc.). Just a few example switches are shown in FIG. 7C, which are controlled by switch control signals S1 and S2 to respectively either connect capacitors C1 and C2 in parallel or in series. Still other switches and switch control signals would be used to establish various connections to capacitors C3 and C4. A few example configurations of the capacitors are shown: for example, a configuration is shown in which all capacitors are connected by the switches in series (forming VH=5Vbat), which configuration is arrived at by setting the switch control signals with particular values. As one skilled will appreciate, the various switch configurations will establish various compliance voltages VH that comprise fractional multiples of the battery voltage. Microcontroller 150, once interrupted, can command the VH generator 76 to use a different switch configuration to adjust the compliance voltage, VH.

When dealing with a VH generator 76 of this type, VH adjustment data 240 may be useful, and as shown may comprise a table relating the compliance voltage VH with a particular battery voltage and switch configuration. Further, data 240 may associate a maximum current, IH(max), with each configuration. The maximum current providable by each capacitor configuration will depend on the size of the capacitances and the manner in which they are connected. This can be important to assist the microcontroller 150 in deciding how to command the VH generator 76.

For example, assume that it is determined that VH should be increased, and that the compliance voltage VH is currently set by the VH generator 76 at 'A', with a switch configuration 3 that establishes VH=2Vbat. In one example, the microcontroller 150 may increase VH by simply commanding the VH generator 76 to use the next-highest switch configuration 4 for VH in VH adjustment data 240—i.e., 'B,' which will increase VH to (7/3)Vbat. However, the microcontroller 150 may also not simply pick the next-highest or lowest switch configuration for the VH generator 76. For example, the microcontroller 150 may realize that stimulation pulses running in the active timing channel(s) are of a relatively large amplitude. If this is the case, commanding the VH generator 76 to use switch configuration 4 ('B') may not be wise, as the maximum current IH(max) producible in this configuration decreases from 2.5 mA ('A') to 2.0 mA ('B'). Commanding the VH generator 76 to use configuration 'B' might run the risk that the compliance voltage VH will become loaded and unable to form the pulses. Thus, the microcontroller 150 may instead command the VH generator 76 to use switch configuration 5 ('C'). This produces an even higher compliance voltage (VH=(5/2) Vbat), but more importantly provides a compliance voltage with a larger maximum current. To summarize, VH adjustment data 240 can include data indicative of the operation of the VH generator 76 to allow the microcontroller 150 to adjust compliance voltage VH in an informed manner.

As shown in FIG. 7A, along with commanding the VH generator 76 how to adjust the compliance voltage VH, the microcontroller block 150 may also issue the window comparator width control signals <W> mentioned earlier. More specifically, the microcontroller block 150 may via bus 192 write values for the control signals <W> to registers included within the compliance detector 201 and compliance logic 220 (FIG. 6A). As mentioned earlier, control signals <W> can be used to set a wide or narrow desired range of acceptable voltages for the window comparators 208p and 208n (FIG. 6B), thus making it respectively less or more likely that high/low signals will be asserted on the bus 210, and hence through operation of the compliance logic 220 (FIG. 6C) that a compliance voltage interrupt Int(VH) will issue.

There are different reasons why the microcontroller 150 may adjust the window comparator width control signals <W>. In one example, the microcontroller 150, after adjusting VH, may initially set <W> to a wide value, and then narrow <W> over time. This will reduce the search time need to establish the compliance voltage VH, and yet deliver an accurate value for VH to save power. In another example, the width may be set based on the amount that VH is adjusted. For example, if a capacitor-based charge pump is used for VH generator 76 (FIG. 7C), VH may be adjusted a small amount—e.g., from (5/4)*Vbat to (4/3)*Vbat, in which case it may only be necessary to widen the comparator windows 208p and 208n by a small amount. By contrast, a larger adjustment, say from 4Vbat to 5Vbat, may warrant widening the comparator windows by a larger amount. The width of the comparator windows may also be scaled in accordance with the battery voltage, Vbat, because VH is ultimately a function of Vbat when a capacitor based charge pump is used. Finally, the number of capacitors used in the charge pump may have an effect on the manner in which the microcontroller 150 sets the width of the comparator windows via control signal <W>. For example, if fewer capacitors were used, the steps in VH creatable by the change pump could be larger, and hence <W> might logically be set to wider values.

While disclosed in the context of a particular design for the stimulation circuitry 170 and DAC circuitry 172, the invention isn't so limited. Also, while disclosed in the context of an implantable pulse generator, the improved compliance voltage monitoring and adjustment circuitry could also be implemented in a non-implantable pulse generator, such as an External Trial Stimulator (ETS). See, e.g., U.S. Pat. No. 9,259,574 (describing an ETS).

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for operating a pulse generator, the pulse generator comprising a plurality of electrode nodes each configured to be coupled to one of a plurality of electrodes in contact with a patient's tissue, and stimulation circuitry powered by an adjustable compliance voltage, the method comprising:
    programming the stimulation circuitry to repetitively provide a train of pulses at selected ones of the electrode nodes, wherein at least one of the pulses in each train has a first amplitude, and wherein other of the pulses in each train have one or more amplitudes different from the first amplitude;
    causing compliance detector circuitry of the pulse generator to take at least one measurement during the at least one pulse having the first amplitude but not during the other of the pulses; and
    using the least one measurement to adjust the compliance voltage.

2. The method of claim 1, wherein the first amplitude comprises a highest amplitude of the pulses in each train.

3. The method of claim 1, wherein the first amplitude and the one or more different amplitudes comprise constant current amplitudes.

4. The method of claim 1, wherein each pulse is represented in the pulse generator by a program, and wherein each program comprises a compliance monitoring bit.

5. The method of claim 4, wherein the compliance monitoring bit is set for each pulse in the train having a first amplitude, and wherein the compliance monitoring bit is not set for the other of the pulses in the train.

6. The method of claim 1, wherein the at least one measurement comprises a voltage measured at each of the selected electrode nodes.

7. The method of claim 6, wherein the selected electrode nodes comprise at least one anodic electrode node and at least one cathodic electrode node.

8. The method of claim 6, wherein at least one of the selected electrode nodes is coupled to a case electrode of the pulse generator.

9. The method of claim 6, wherein the compliance detector circuitry receives the voltages measured at each of the selected electrode nodes.

10. The method of claim 9, wherein the voltages comprise at least one anodic voltage received from at least one of the electrode nodes selected as an anode, and at least one cathodic voltage received from at least one of the electrode nodes selected as a cathode.

11. The method of claim 10, wherein the compliance detector circuitry produces an anode low signal and an anode high signal for each of the one or more anode electrode nodes, and produces a cathode low signal and a cathode high signal for each of the one or more cathode electrode nodes.

12. The method of claim 1, wherein compliance logic of the pulse generator uses the anode low, the anode high, the cathode low, and the cathode high signals to adjust the compliance voltage.

13. The method of claim 11, wherein the compliance detector circuitry comprises comparator circuitry for producing the anode low, the anode high, the cathode low, and the cathode high signals.

14. The method of claim 11, wherein the compliance detector circuitry asserts,
    for each anode electrode node,
        the anode low signal if the voltage received from that anode electrode node is below a first reference voltage,
        the anode high signal if the voltage received from that anode electrode node is above a second reference voltage,
    for each cathode electrode node,
        the cathode low signal if the voltage received from that cathode electrode node is below a third reference voltage, the cathode high signal if the voltage received from that cathode electrode node is above a fourth reference voltage.

15. The method of claim 11, wherein the compliance detector circuitry comprises anode comparator circuitry for producing the anode low and the anode high signals, and cathode comparator circuitry for producing the cathode low and the cathode high signals.

16. The method of claim 15, wherein the anode comparator circuitry comprises a first comparator for producing the anode low signal and a second comparator for producing the anode high signal, and wherein the cathode comparator circuitry comprises a third comparator for producing the cathode low signal and a fourth comparator for producing the cathode high signal.

17. The method of claim 1, wherein the stimulation circuitry comprises current source circuitry coupled to the compliance voltage, and current sink circuitry is coupled to ground.

18. The method of claim 17, wherein the train of pulses at the selected ones of the electrode nodes comprises an anodic current formed by the current source circuitry at one or more anodic electrode nodes, and a cathodic current formed by the current sink circuitry at one or more cathodic electrode nodes.

19. The method of claim 18, wherein the current source circuitry comprises first digital-to-analog converter (DAC) circuitry digitally controlled to source the anodic current to the one or more anodic electrode nodes, and wherein the current sink circuitry comprises second digital-to-analog converter (DAC) circuitry digitally controlled to sink the cathodic current from the one or more cathodic electrode nodes.

20. The method of claim 19, wherein the pulse generator comprises a spinal cord stimulator or a deep brain stimulator.

* * * * *